(12) United States Patent
Lupo, Jr. et al.

(10) Patent No.: US 6,200,254 B1
(45) Date of Patent: Mar. 13, 2001

(54) MACROCYCLIC KETONES AS FRAGRANCE MATERIALS AND METHODS FOR MAKING SAME

(75) Inventors: Andrew T. Lupo, Jr., Emerson, NJ (US); Tetsuo Nakatsu, Chappaqua, NY (US); John Caldwell, Hewitt; Michael E. Lankin, Cedar Grove, both of NJ (US); Carter B. Green, Stony Point, NY (US); Takashi Aida, Chigasaki (JP)

(73) Assignees: Takasago International Corporation (JP); Takasago Institute for Interdisciplinary Science, Inc., Rockleigh, NJ (US)

( * ) Notice: Subject to any disclaimer, the term of this patent is extended or adjusted under 35 U.S.C. 154(b) by 0 days.

(21) Appl. No.: 09/316,722

(22) Filed: May 21, 1999

(51) Int. Cl.⁷ .............................. A61K 7/46; C07C 49/607
(52) U.S. Cl. .................................. 572/8; 512/27; 568/338; 568/375; 568/343
(58) Field of Search ........................... 572/8, 27; 568/338, 568/375, 343

(56) References Cited

U.S. PATENT DOCUMENTS

| | | | | |
|---|---|---|---|---|
| 3,778,483 | * | 12/1973 | Becker et al. | 512/8 |
| 4,346,023 | * | 8/1982 | Buchi et al. | 512/8 |
| 5,354,735 | * | 10/1994 | Demole et al. | 512/8 |

OTHER PUBLICATIONS

S.Arctander, Perfume and Flavor Chemicals, vol. 1, Section 700, 1969.*

* cited by examiner

Primary Examiner—Sreeni Padmanabhan
(74) Attorney, Agent, or Firm—Morrison Law Firm

(57) ABSTRACT

Novel macrocyclic diene ketone compounds useful as fragrance materials are described having the following general formula (I):

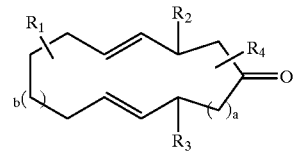

(I)

where $R_1$, $R_2$, $R_3$ and $R_4$ are each either a hydrogen atom or a $C_1$ to $C_4$ alkyl, a is the integer 1 or 2 and b is an integer in a range from 1 to 6. Novel pathways are described for synthesizing these macrocyclic diene ketones, as well as saturated and mono-unsaturated macrocyclic ketones having the following general formula (IV):

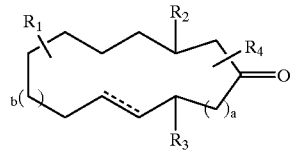

(IV)

where $R_1$, $R_2$, $R_3$ and $R_4$ are each independently a hydrogen atom or a $C_1$ to $C_4$ alkyl, a is the integer 1 or 2 and b is an integer in a range from 1 to 6.

35 Claims, No Drawings

MACROCYCLIC KETONES AS FRAGRANCE MATERIALS AND METHODS FOR MAKING SAME

BACKGROUND OF THE INVENTION

The present invention relates to novel macrocyclic diene ketone compounds having unique fragrance qualities. These compounds are suitable for use in fragrance applications.

Some macrocyclic ketones (ring sizes of 15–17) are used quite extensively in the field of perfumery as musk odorants. For example, a fully saturated macrocyclic ketone, exaltone (cyclopentadecanone), is reported in S. Arctander, "Perfume and Flavor Chemicals, Vol. I," sec. 813, (1969). Similarly, muscone (3-methylcyclopentadecanone) is reported in S. Arctander, "Perfume and Flavor Chemicals, Vol. II," sec. 2276, (1969). Several mono-unsaturated macrocyclic ketones are also known in the field of perfumery. Some examples include civetone (cycloheptadec-9-en-1-one) as reported in S. Arctander, "Perfume and Flavor Chemicals, Vol. I," sec. 700, (1969); and ambretone (cyclohexadec-5-en-1-one), reported in T. Kato et al., "Bull. Chem. Soc. Jpn.," vol. 53 p. 2958 (1980) and 3-methylcyclopentadec-5-en-1-one as disclosed by E. Demole et al., U.S. Pat. No. 5,354,735.

In contrast, doubly unsaturated macrocyclic ketones (cycloalkadienones) are not extensively used in the creation of fragrances for perfumes and consumer products. Several reports describing the syntheses and the potential use in fragrances of a few examples of cycloalkadienones have appeared in the literature but synthetic and other practical considerations have precluded their use in commercial fragrance applications. All examples of cycloalkadienones pertinent to a discussion of the prior art related to this invention are illustrated below:

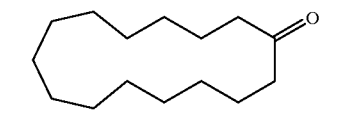

I

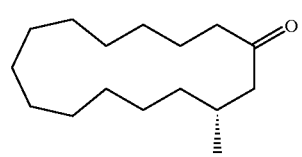

II

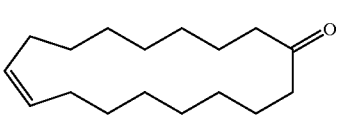

III

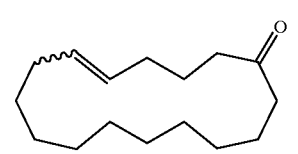

IV

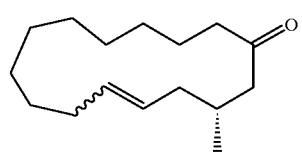

V

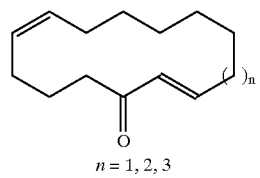

$n = 1, 2, 3$

VI

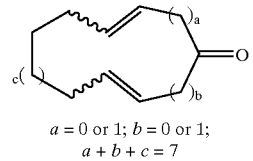

$a = 0$ or $1$; $b = 0$ or $1$;
$a + b + c = 7$

VII

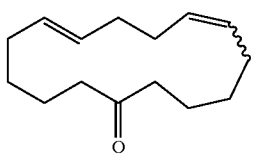

VIII

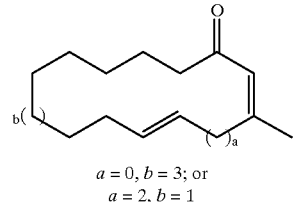

$a = 0, b = 3$; or
$a = 2, b = 1$

IX

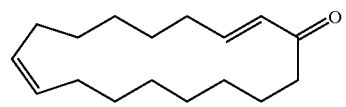

X

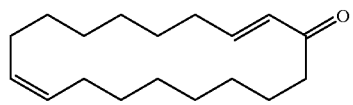

XI

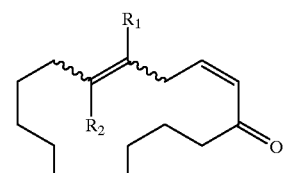

$R_1 = CH_3, R_2 = H$ or
$R_1 = H, R_2 = CH_3$

XII

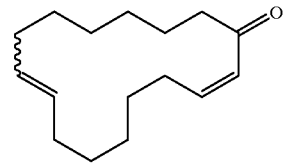

XII

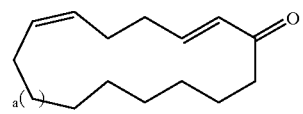

XIII

Most examples include the α,β-unsaturated enone moiety (not present in the materials of this invention) prepared via a variety of techniques including phosphonate Wittig reactions. See, for example, H. J. Bestmann and H. Luetke, "Tetrahedron Lett." vol. 25, pp. 1707–10 (1984). See also, K. C. Nicolaou et al. "J. Org. Chem." vol. 44, pp. 4011–13 (1979). Additional references showing phosphonate Wittig reactions include G. Buchi and H. Wuest, "Helv. Chim. Acta." vol 62, pp. 2661–72 (1979), G. Buchi and H. Wuest, U.S. Pat. No. 4,346,023, G. Buchi and H. Wuest, U.S. Pat. No. 4,302,607, G. Buchi and H. Wuest, European Patent No. 15,412, G. Buchi and H. Wuest, Japanese Patent No. JP 55,111,438 and K. C. Nicolaou et al. "J. Am. Chem. Soc." vol. 120, pp. 5132–5133 (1998). Other methods for preparing cycloalkadienones via ring expansion techniques have also been reported. See J. Tsuji et al. "J. Org. Chem." vol. 45, pp. 5209–11 (1980). See also Japanese Patent No. JP 59,029, 687 A2 and S. Sakane et al. "Tetrahedron Lett." vol. 24, pp. 943–6 (1983). In addition, see Bluthe et al. "Tetrahedron" vol.42, pp. 1333–44 (1986), N. Bluthe et al. European Patent No. EP 127536 A1, N. Bluthe et al. "Tetrahedron Lett." vol. 25(27), pp. 2873–6(1984). Other miscellaneous methods are also reported. See, for example, B. D. Mookherjee et al. "J. Org. Chem." vol. 36, pp. 3266–70 (1971), Japanese Patent No. JP 06092894 A2 (1994), R. N. Majee et al. "Indian Perfum." vol. 35, pp. 239–40 (1991) and T. Ikuta and Y. Mizoe, Japanese Patent No. JP 52118447 (1977). Both the structures and the methods of preparation of all of these materials clearly differentiate this prior art from the materials and processes encompassed by the present invention.

The present invention also relates to novel synthesis pathways for obtaining macrocyclic diene ketones as well as saturated and mono-unsaturated macrocyclic ketones. Individual reaction steps used in the processes of the present invention have been previously disclosed. Grignard reactions are reported, for example, in D. A. Shirley, "Organic Reactions" vol. 8 p. 28 (1954); C. Blomberg and F. A. Hartog, "Synthesis" p. 18 (1977) and R. G. Woolford, "J. Org. Chem." vol. 23, p. 2042 (1958). Claisen rearrangements are reported, for example, in S. J. Rhoads, "Organic Reactions" vol. 22, p. 1 (1975) and G. B. Bennett, "Synthesis" p. 539 (1977). Acyloin condensations are reported, for example, in J. J. Bloomfield and D. C. Owsley, "Organic Reactions" vol.23, p.259 (1976); K. T. Finley, "Chem. Revs." vol. 64, p. 573 (1964), K. Ruhlmann, "Synthesis" p. 236 (1971), U.S. Pat. No. 2,529,825 and U.S. Pat. No. 2,228,268. Dieckman cyclizations are reported, for example, in P. S. Pinkney, "Org. Syn. Coll." vol. 2, p. 116 (1943), J. P. Schaefer and J. J. Bloomfield, "Organic Reactions" vol. 15, p. 1 (1967) and N. J. Leonard and C. W. Schimelpfenig Jr., "J. Org. Chem." vol. 23, p. 1708 (1958). However, it is the novel sequence of reactions as well as the unique nature of the substrate materials upon which they act, that comprises the novel processes of the invention.

Herein we describe a previously undisclosed group of cycloalkadienones, which we have shown to have unique fragrance qualities suitable for use in fragrance applications. In addition, we also disclose novel, practical synthetic routes to these materials in Examples 1–4. Additionally, we disclose novel, practical synthetic routes to saturated and mono-unsaturated macrocyclic ketones in Example 5.

OBJECTS AND SUMMARY OF THE INVENTION

It is an object of the present invention to provide novel compounds of the general Formula (I):

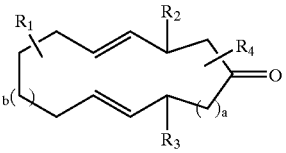

(I)

wherein $R_1$, $R_2$, $R_3$ and $R_4$ are independently a hydrogen atom or a $C_1$ to $C_4$ alkyl, a is the integer 1 or 2 and b is an integer in a range from 1 to 6. Preferably, $R_1$, $R_2$, $R_3$, and $R_4$ are independently H or $CH_3$. Preferably, a is the integer 1 or 2, and b is an integer in a range from 2 to 5.

It is a further object of the present invention to provide previously undisclosed cycloalkadienones, which we have shown to have unique fragrance qualities suitable for use in fragrance applications.

It is a further object of the present invention to provide fragrance compositions using novel cycloalkadienones.

It is a further object of the present invention to provide novel, practical synthetic routes to cycloalkadienones.

It is a further object of the present invention to provide novel, practical synthetic routes to saturated and mono-unsaturated macrocyclic ketones.

The term "$C_1$ to $C_4$ alkyl" is defined to include straight or branched, saturated or unsaturated carbon chains having from 1 to 4 carbon atoms. Examples of a $C_1$ to $C_4$ alkyl group include methyl, ethyl, allyl, propyl, iso-propyl, butyl, iso-butyl, and tert-butyl.

DETAILED DESCRIPTION OF THE PREFERRED EMBODIMENTS

The processes of the present invention are variations on a central theme of synthesis, namely the Claisen rearrangement of bis allyl alcohols (prepared via Grignard reagents with aldehydes) followed by a ring cyclization reaction (either acyloin condensation or Dieckmann cyclization) and subsequent reduction (acyloin pathway) or decarboalkoxylation (Dieckmann pathway) to produce the target macrocyclic diene ketones.

EXAMPLE 1

(E1): Process 1

The process of Example 1 is illustrated below:

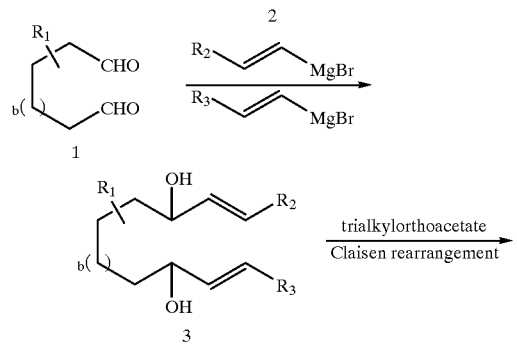

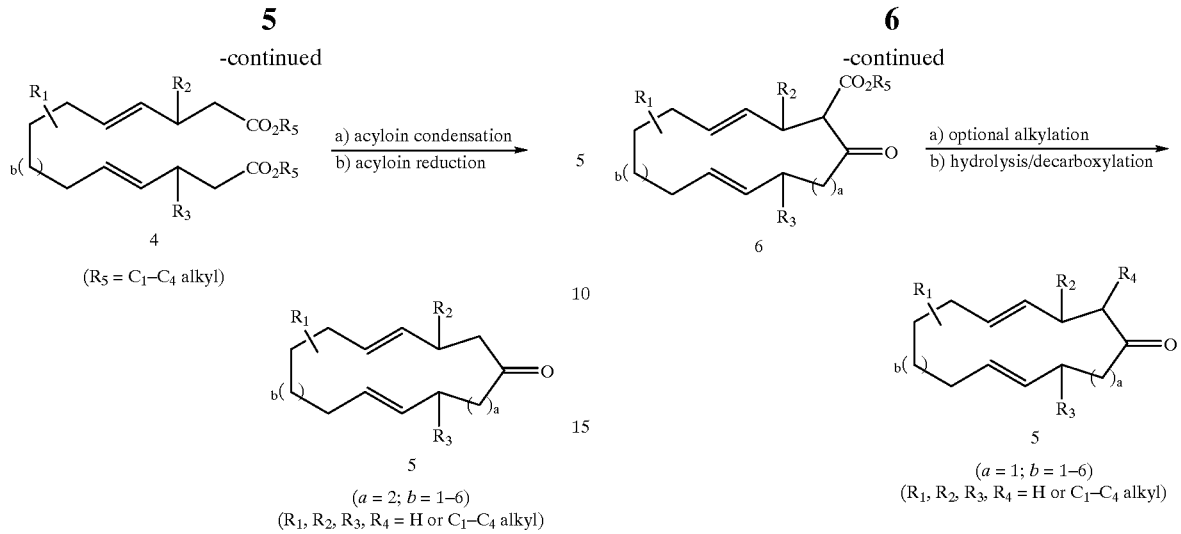

(R5 = C1–C4 alkyl)

(a = 2; b = 1–6)
(R1, R2, R3, R4 = H or C1–C4 alkyl)

An optionally substituted 1,ω-dialdehyde 1 is treated with Grignard reagent 2 to give bis-allyl alcohol 3. If $R_2$ is not equal to $R_3$, then a mixture of Grignard reagents is used to give a mixture of bis-allyl alcohols 3 which can be separated by standard techniques familiar to those skilled in the art. Treatment of the bis-allyl alcohol 3 with a trialkylorthoacetate in the presence of acid catalysis results in a bis-Claisen rearrangement providing the linear bis-ester 4. Acyloin condensation of bis-ester 4 followed by reduction of the α-hydroxyketone (acyloin) produced provides the desired target cycloalkadienone 5.

EXAMPLE 2

(E2): Process 2

The process of Example 2 is illustrated below:

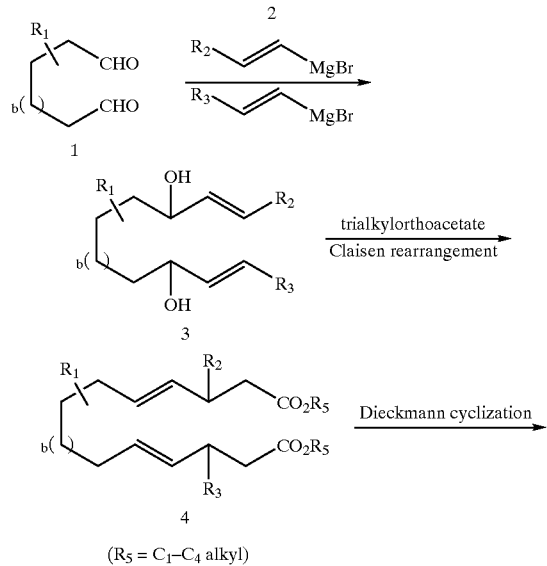

(R5 = C1–C4 alkyl)

(a = 1; b = 1–6)
(R1, R2, R3, R4 = H or C1–C4 alkyl)

Treatment of the linear bis-ester 4 (as prepared in Process 1) under conditions of a Dieckmann cyclization provides the β-ketoester 6. The β-ketoester 6 can be optionally alkylated and then treated under conditions which results in the hydrolysis and decarboxylation of the carboalkoxy group providing the desired target cycloalkadienone 5.

EXAMPLE 3

(E3): Process 3

The process of Example 3 is illustrated below:

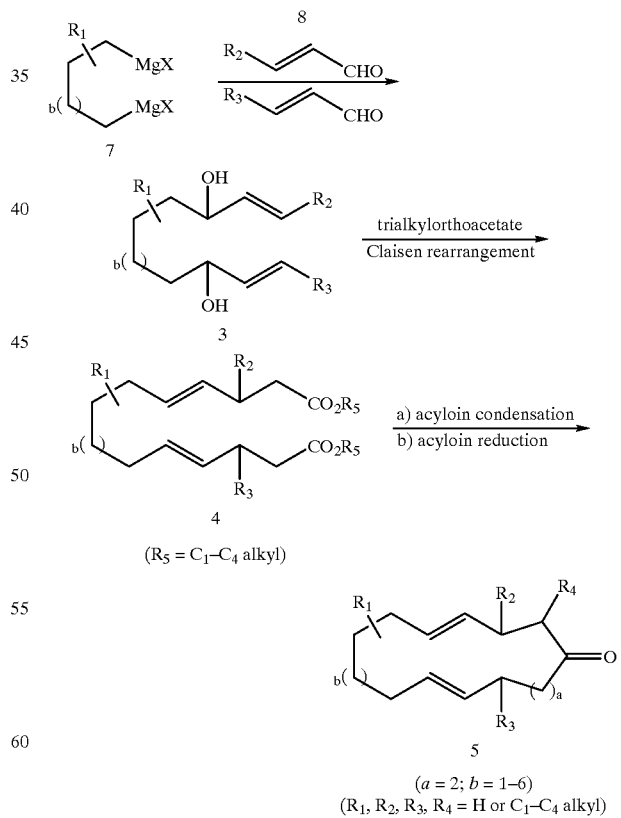

(R5 = C1–C4 alkyl)

(a = 2; b = 1–6)
(R1, R2, R3, R4 = H or C1–C4 alkyl)

The 1,ω-di-Grignard reagents 7, prepared from the corresponding, optionally substituted, dihalides, are reacted with unsaturated aldehyde 8 to give bis-allyl alcohol 3. If $R_2$ is not equal to $R_3$ then a mixture of aldehydes 8 is used to give a mixture of bis-allyl alcohols 3 which can be separated by standard techniques farmiliar to those skilled in the art. The remainder of the steps outlined in Process 1 can then be followed to provide the desired target cycloalkadienone 5. Namely, Claisen rearrangement of bis-allyl alcohol 3 provides the bis-ester 4. Acyloin condensation and subsequent reduction ofthe resulting α-hydroxyketone provides the target cycloalkadienone 5.

EXAMPLE 4

(E4): Process 4

The process of Example 4 is illustrated below:

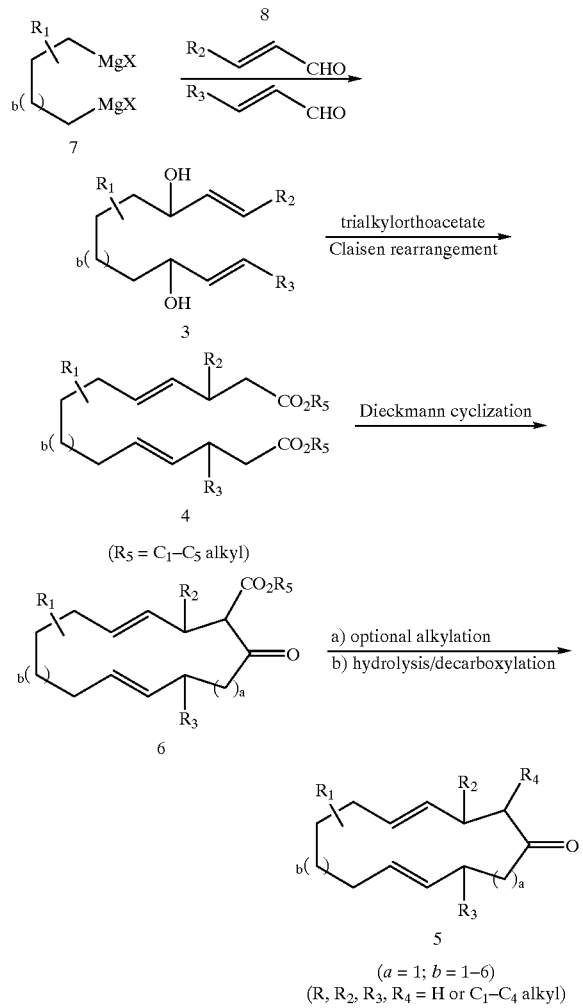

The bis-allyl alcohol 3 is prepared as described in Process 3. The remainder of the steps outlined in Process 2 can then be followed to provide the desired target cycloalkadienone 5. Namely, Dieckman cyclization of bis ester 4 to give the ketoester 6, optional alkylation, and then hydrolysis/decarboxylation provides the target cycloalkadienone 5.

EXAMPLE 5

(E5): Process 5

The processes of Example 5 are illustrated below:

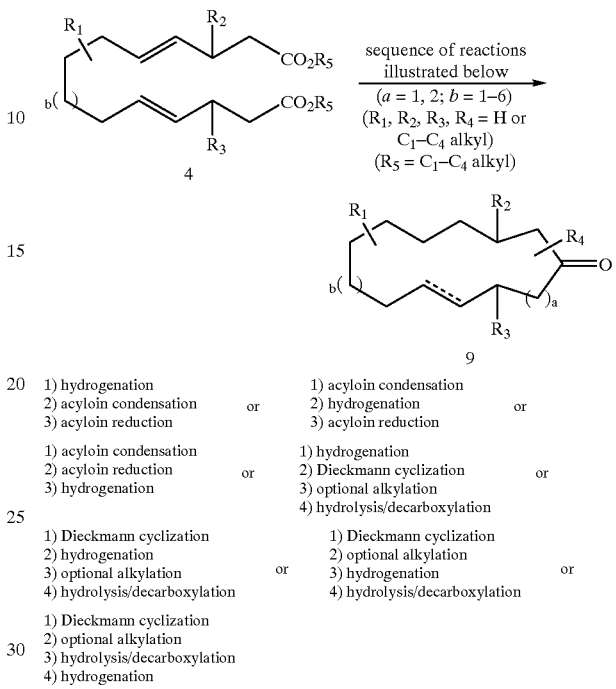

Optional hydrogenation (complete or partial) of any intermediate produced in Processes 1, 2, 3, and 4 can be performed subsequent to the Claisen rearrangement step (preparation of the linear bis-ester intermediate 4). Completion of the remaining steps of the Processes 1, 2, 3, and 4 as outlined above, can be then be used for the preparation of saturated (complete hydrogenation) and mono-unsaturated (partial hydrogenation) macrocyclic ketones.

EXAMPLE 6

(E6)—cyclohexadeca-4E,12E-dien-1-one

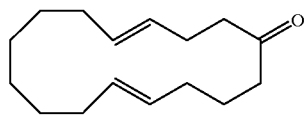

E6-Step 1: Preparation of octane-1,8-dial:

To a heterogeneous mixture of octane-1,8-diol (94.64 g, 0.648 mole), TEMPO (5.08 g, 0.038 mole, available from Aldrich Chemical Company, Milwaukee, Wis.), potassium bromide (3.90 g, 0.033 mole), sodium phosphate (7.80 g, 0.065 mole), disodium phosphate (9.24 g, 0.065 mole) in methylene chloride (1.3 L) and water (500 ml) was added dropwise 12% aqueous sodium hypochlorite (1,225 g) slowly over 2 hours while maintaining the temperature below 35° C. The reaction was stirred for an additional 30 minutes and the two layers were separated. The aqueous layer was extracted with methylene chloride and combined with the organic layer. The combined organic layer was washed with saturated aqueous sodium bicarbonate, saturated aqueous sodium chloride and water. The organic fraction was dried over sodium sulfate, filtered and evaporated. The material was vacuum distilled 82–84° C./0.5 mm Hg to afford octane-1,8-dial (92 g, 100% yield). $C_8H_{14}O_2$ (142.20 g/mole). bp: 82° C./0.55 mm Hg. $^1$HNMR (500 MHz, CDCl$_3$): 1.35 (m, 4H), 1.63 (m, 4H), 2.43 (m, 4H), 9.76 (t, 2H) ppm. $^{13}$CNMR (125 MHz, CDCl$_3$): 21.8, 28.9, 43.8, 202.7 ppm. IR ($v_{max}$(cm$^{-1}$)): 2940, 2860, 2740, 1725, 1460, 1420, 1400. MS (m/z): 24(M-18), 98, 95, 81, 67, 57, 54, 44, 41.

E6-Step 2: Preparation of dodeca-1,11-diene-3,10-diol

Method A: To a 2 liter round bottomed Morton flask containing magnesium (56.88 g, 2.34 mole) and diethyl ether (50 ml) was added 1,6-dibromohexane (266.16 g, 1.09 mole) very slowly at first to initiate the Grignard reaction. During the addition the reaction was vigorously stirred with a mechanical stirrer under dry nitrogen gas. After the reaction was initiated, diethyl ether (650 ml) was added to the remaining 1,6-dibromohexane and the addition was continued over 2 hours while maintaining reflux. The heat was removed and a solution of freshly distilled acrolein (123 g, 2.20 mole) in diethyl ether (300 ml) was added over 2 hours. The reaction was stirred overnight and to the reaction mixture was added saturated aqueous ammonium chloride (1000 ml). The reaction was acidified with hydrochloric acid, and the aqueous layer was extracted with ether. The combined organic layers were washed 2 times with saturated aqueous sodium bicarbonate, saturated aqueous sodium chloride, water, dried with magnesium sulfate, filtered and evaporated under reduced pressure to afford an oil. The lower boiling impurities were removed under vacuum (0.7 mm Hg) (the bath temperature not exceeding 100° C.) to afford dodeca-1,11-diene-3,10-diol (92 g, 44% yield) as a aviscous oil which was suitable for use in the subsequent reaction.

Method B: A solution of octane-1,8-dial (44.0 g, 0.38 mole) in tetrahydrofuran (170 ml) was added to a solution of vinylmagnesium bromide (800 ml, 1M, 0.80 moles) in tetrahydrofuran at 0° C. over 1 hour. The reaction mixture was warmed to room temperature and stirred for 2 hours during which time a heavy precipitate formed. The reaction was poured onto saturated aqueous ammonium chloride (500 ml) extracted with ether, washed with saturated aqueous sodium bicarbonate, brine, 10% aqueous hydrochloric acid and water. The organic layer was dried with magnesium sulfate, filtered and evaporated to afford dodeca-1,11-diene-3,10-diol (58 g, 90% yield) as a viscous orange oil which was suitable for use in the subsequent reaction. $C_{12}H_{22}O_2$ (198.31 g/mole). $^1$HNMR (500 MHz, CDCl$_3$): 0.85 (m, 1H), 1.10–1.60 (m, 11H), 4.08 (q, 2H), 5.15 (dd, 4H), 5.85 (m, 2H) ppm. $^{13}$CNMR (125 MHz, CDCl$_3$): 25.2, 29.5, 37.0, 73.2, 114.5, 141.4 ppm. IR ($v_{max}$(cm$^{-1}$)): 3350(bs), 2940(s), 2850(s), 1650(w), 1460(m), 1420(m), 1000(s), 920(s), 720 (s). MS (m/z): 151, 133, 123, 109, 95, 81, 67, 57, 41.

E6-Step 3: Preparation of diethyl hexadeca-4E,12E-diene-1,16-dioate:

A mixture of of dodeca-1,11-diene-3,10-diol (39.4 g, 200 mmole), triethyl orthoacetate (550 ml, 3.0 mole), and propionic acid (1.18 g, 16 mmole) was heated to 120–140° C. for 1.5 hours with the slow distillation ofthe ethanol formed during the reaction. The solution was cooled to 80° C. and the lower boiling materials were removed by vacuum distillation to afford diethyl hexadeca-4E,12E-diene-1,16-dioate (62 g, 93% yield) as an oil which was suitable for use in the subsequent reaction. If desired, the material can be purified via reduced pressure distillation (150–155° C./0.1 mm Hg). $C_{20}H_{34}O_4$ (338.49 g/mol). bp: 178° C./10.7 mm Hg. HNMR (500 MHz, CDCl$_3$): 1.25 (m, 16H), 1.90 (m, 4H), 2.30 (m, 8H), 4.10 (q, 2H), 5.40 (m, 4H) ppm. $^{13}$CNMR (125 MHz, CDCl$_3$): 14.3, 28.0, 29.0, 29.4, 32.5, 34.5, 60.2, 128.0, 131.8, 173.3 ppm. IR ($v_{max}$(cm$^{-1}$)): 2940, 2850, 1740, 1450, 1380, 1250, 1180, 1040, 970. MS (m/z): 338 (M$^+$), 292, 247, 176, 163, 149, 135, 121, 107, 95, 81, 67, 55,41.

E6-Step 4: Preparation of 16-hydroxycyclohexadeca-4E,12E-dien-1-one:

In a 2 L Morton flask a mixture of sodium (7.48 g, 0.34 mole) in toluene (600 ml) was heated to reflux and stirred vigorously for 1 hour. To this solution was added dropwise (very slowly) a mixture of diethyl hexadeca-4E,12E-diene-1,16-dioate (24.86 g, 0.073 mole) and chlorotrimethylsilane (41.7 ml, 0.33 mole) in toluene (100 ml) over 2 hours. The reaction was heated to reflux for an additional 4 hours, then cooled to room temperature and stirred for an additional 16 hours. To the reaction mixture was added methanol (~100 ml), the mixture is stirred 1 hour, and then left to stand for 1 hour. The resulting bi-phasic mixture was separated and the top layer is washed with 10% aqueous hydrochloric acid. The aqueous wash was re-extracted with ether and the organic layers are combined. The bottom layer from the bi-phasic mixture described above was combined with the aqueous wash and extracted again with diethyl ether. All organic layers were combined, dried with magnesium sulfate, filtered and evaporated to give the 16-hydroxycyclohexadeca-4E,12E-dien-1-one (20.0 g, 93% yield) as a brown oil which can be used directly in the next step. If desired, the material can be purified via reduced pressure distillation (210–220° C./0.3 mm Hg). $C_{16}H_{26}O_2$ (250.38 g/mole). bp. 210–220° C./0.3 mm Hg. HNMR (500 MHz, CDCl$_3$): 1.20–1.80 (m, 10H), 1.90–2.09 (m, 4H), 2.10–2.30 (m, 4H) 2.35 (m, 2H), 2.50 (m, 2H), 4.10 (m, 1H), 5.40 (m, 4H) ppm. $^{13}$CNMR (125 MHz, CDCl$_3$): 27.8, 27.9*, 28.1, 28.5*, 31.4, 31.5, 32.8, 37.9, 76.2, 127.6, 128.8, 132.6, 133.1, 214 ppm. IR ($v_{max}$(cm$^{-1}$)): 3450(b), 2940(s), 2910(s), 2850(s), 1720(s), 1440(m), 970(s). MS(m/z): 250 (M$^+$), 232, 221, 203, 189, 176, 161, 149, 135, 121, 109, 95, 81, 67, 55, 41.

E6-Step 5: Preparation of cyclohexadeca-4E,12E-dien-1-one:

To a flask containing a solution of 16-hydroxycyclohexadeca-4E,12E-dien-1-one (2.5 g, 10 mmole), triethylamine (2.02 g, 20 mmole) in 1,4-dioxane (20 ml) was added chlorotrimethylsilane (2.17 g, 20 mmole) in one portion at room temperature. The reaction was stirred for 18 hours and then quickly filtered through a fritted glass fimnel. The resultant solution of the silyl ether was transferred to a pressure-equalizing dropping funnel and used directly in the following operations. A 2-neck round bottomed flask was charged with sodium (460 mg, 20 mmole), chlorotrimethylsilane (2.17 g, 20 mmole) and 1,4-dioxane (15 ml) and the mixture was warmed to 45° C. The solution of the silyl ether prepared above was added slowly (30 minutes via a pressure-equalizing dropping funnel) while gradually increasing the reaction temperature to 110° C. The mixture was stirred at 110° C. for 16 hours, cooled to room temperature, and to the mixture was added methanol. The reaction mixture was poured onto water, extracted with ether, dried with sodium sulfate, filtered and evaporated to give the crude ketone product. This material was purified by chromatography (CH$_2$Cl$_2$) to afford cyclohexadeca-4E,12E-dien-1-one (1.24 g, 53% yield) as a colorless liquid. $C_{16}H_{26}O$ (234.39 g/mole). $^1$HNMR (500 MHz, CDCl$_3$): 1.21 (m, 4H), 1.34 (m, 4H), 1.61 (m, 2H), 1.97 (m, 4H), 2.03 (q, 2H), 2.28 (m, 2H), 2.39 (m, 4H), 5.28 (m, 1H), 5.34 (m, 3H) ppm. $^{13}$CNMR (125 MHz, CDCl$_3$): 22.3, 26.8, 27.0, 27.6, 28.1, 28.9, 30.8, 30.9, 31.4, 41.4, 42.8, 128.9, 129.3, 131.4, 132.1, 211.6 ppm. IR ($v_{max}(cm^{-1})$): 2950(s), 2920(s), 2860(s), 1715(s), 1440(m), 1260(s), 980(s), 800(s). MS (m/z): 234(M$^+$), 216, 205, 191, 177, 163, 149, 135, 123, 109, 95, 81, 67, 55, 41.

EXAMPLE 7

(E7): cyclopentadeca-4E,11E-dien-1-one

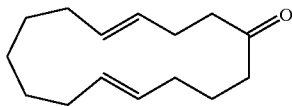

E7-Step 1: Preparation of heptane-1,7-dial:

Heptane-1,7-diol (75 g, 590 mmole) was treated as described in Example 6 (step 1) to give heptane-1,7-dial (72 g, 100% yield). $C_7H_{12}O_2$ (128.17 g/mole). bp: 50° C./0.18 mm Hg. $^1$HNMR (500 MHz, CDCl$_3$): 1.36 (m, 2H), 1.66 (p, 4H), 2.46 (dt, 4H), 9.76 (t, 2H) ppm. $^{13}$CNMR (125 MHz, CDCl$_3$): 21.8, 28.6, 43.6, 202.3 ppm. IR ($v_{max}(cm^{-1})$): 2950, 2870, 2740, 1725, 1460, 1420, 1400. MS (m/z): 110(M-18), 95, 84, 81, 71, 67, 57, 44, 41.

E7-Step 2: Preparation of undeca-1,10-diene3,9-diol:

Heptane-1,7-dial (97.3 g, 530 mmole) was treated as described in Example 6 (Step 2/Method B) to give undeca-1,10-diene-3,9-diol (110 g, 63% yield). $C_{11}H_{20}O_2$ (184.28 g/mole). $^1$HNMR (500 MHz, CDCl$_3$): 0.85 (m, 2H), 1.20–1.40 (m, 6H), 1.50 (m, 2H), 4.08 (m, 2H), 5.07 (d, 2H), 5.20 (d, 2H), 5.84 (m, 2H) ppm. $^{13}$CNMR (125 MHz, CDCl$_3$): 25.29, 29.49, 37.00, 73.24, 114.60, 141.37 ppm. IR ($v_{max}(cm^{-1})$): 3350, 2950, 2850, 1640, 1420, 920. MS (m/z): 165(M-19), 137, 110, 95, 81, 67, 57, 41.

E7-Step 3: Preparation of diethyl pentadeca-4E,11E-diene-1,15-dioate:

Undeca-1,10-diene-3,9-diol (73.6 g, 230 mmole) was treated as described in Example 6 (Step 3) to give diethyl pentadeca-4E,11E-diene-1,15-dioate (74 g, 57% yield). $C_{19}H_{32}O_4$ (324 g/mole). bp: 190° C./2.0 mm Hg. $^1$HNMR (500 MHz, CDCl$_3$): 1.25 (m, 12H), 1.93 (m, 4H), 2.32 (m, 8H), 4.10 (q, 4H), 5.43 (m, 4H) ppm. $^{13}$CNMR (125 MHz, CDCl$_3$): 14.3, 28.0, 28.7, 29.4, 32.5, 34.5, 60.3, 127.9, 131.8, 173.4 ppm. IR ($v_{max}(cm^{-1})$): 2980, 2940, 2850, 1740, 1440, 1380, 1060, 970. MS (m/z): 324(M$^+$), 278, 233, 204, 162, 149, 135, 121, 107, 95, 88, 81, 67, 55, 41.

E7-Step 4: Preparation of 15-hydroxycyclopentadeca-4E, 11E-dien-1-one:

Diethyl pentadeca-4E,11E-diene-1,15-dioate (23.78 g, 100 nmmole) was treated as described in Example 6 (Step 4) to give 15-hydroxycyclopentadeca-4E,11E-dien-1-one (13.0 g, 75% yield). $C_{15}H_{24}O_2$ (236.36 g/mole). $^1$HNMR (500 MHz, CDCl$_3$): 1.10–1.45 (m, 6H), 1.80 (m, 1H), 1.90–2.10 (m, 4H), 2.11 (m, 1H), 2.25 (m, 3H), 2.38 (m, 2H), 2.54 (m, 1H), 3.43 (d, 1H, J=4.6 Hz), 4.14 (ddd, 1H, J=4.6 Hz), 5.30–5.47 (m,4H) ppm. $^{13}$CNMR (125 MHz, CDCl$_3$): 27.1, 27.8, 27.9, 28.0, 29.7, 32.0, 32.4, 32.6, 38.1, 76.0, 128.7, 128.9, 132.9, 133.9, 211.6 ppm. IR ($v_{max}(cm^{-1})$): 3430(bw), 2940(s), 2850(s), 1720(s), 1460(m), 1440(m), 1380(m), 1250(m), 970(s), 840(m). MS (m/z): 236(M$^+$), 218, 207, 189, 175, 162, 149, 135, 121, 109, 95, 81, 67, 55, 41.

E7 Step 5: Preparation of cyclopentadeca-4E,11E-dien-1-one:

15-Hydroxycyclopentadeca-4E,11E-dien-1-one (1.38 g, 6.26 mmole) was treated as described in Example 6 (Step 5) to give cyclopentadeca-4E,11E-dien-1-one (0.80 g, 62% yield). $C_{15}H_{24}O$ (220.36 g/mole). $^1$HNMR (500 MHz, CDCl$_3$): 1.15 (m, 2H), 1.22–1.39 (m, 5H), 1.63 (m, 2H), 2.00 (m, 6H), 2.29 (m, 2H), 2.41 (m, 3H), 5.25 (m, 2H), 5.34 (m, 2H) ppm. $^{13}$CNMR (125 MHz, CDCl$_3$): 21.8, 26.5, 28.0, 28.1*, 30.7, 31.9, 32.0, 42.5, 42.9, 129.2, 130.3, 132.2, 132.3, 212.5 ppm. IR ($v_{max}(cm^{-1})$): 2950(s), 2920(s), 2860(s), 1715(s), 1440(m), 1370(m), 970(s). MS (m/z): 220(M$^+$), 202, 191, 177, 152, 135, 123, 109, 95, 79, 67, 55, 41.

EXAMPLE 8

(E8): cyclotetradeca-4E,10E-dien-1-one

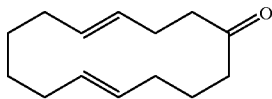

E8-Step 1: Preparation of hexane-1,6-dial:

Hexane-1,6-diol (103.25 g, 875 mmole) was treated as described in Example 6 (Step 1) to give hexane-1,6-dial (74 g, 74% yield). $C_6H_{10}O_2$ (114 g/mol). bp: 105–106° C./1 mm Hg. (lit. bp: 92° C./1.2 mm Hg). $^1$HNMR (500 MHz, CDCl$_3$): 1.80 (m, 4H), 2.55 (m, 4H), 9.88 (s, 2H) ppm. $^{13}$CNMR (125 MHz, CDCl$_3$): 21.8, 43.9, 202.2 ppm. IR ($v_{max}(cm^{-1})$): 2920(s), 2850(s), 2730(w), 1720(s), 1460(m), 1170(m), 1120(s), 1000(m), 940(m). MS (m/z): 114(M$^+$), 96, 70, 57, 44, 41, 39.

E8-Step 2: Preparation of deca-1,9-diene-3,8-diol:

Hexane-1,6-dial (44 g, 386 mmole) was treated as described in Example 6 (Step 2/Method B) to give deca-1,9-diene-3,8-diol (58 g, 88% yield). $C_{10}H_{18}O_2$ (170 g/mole). bp: 114° C./1.5 mm Hg). $^1$HNMR (500 MHz, CDCl$_3$): 1.35 (m, 4H), 1.45 (m, 4H), 4.05 (m, 2H), 5.06 (d, 2H), 5.18 (d, 2H), 5.80 (m, 2H) ppm. $^{13}$CNMR (125 MHz, CDCl$_3$): 25.2, 36.9, 73.0, 114.6, 141.3 ppm. IR ($v_{max}(cm^{-1})$): 3350(bs), 3080(w), 2940(s), 2860(s), 1640(w), 1420(s), 990(s), 920(s). MS (m/z) 152(M-18), 137, 123, 109, 95, 81, 67, 57, 54, 41.

E8-Step 3: Preparation of diethyl tetradeca-4E,10E-diene-1,14-dioate:

Deca-1,9-diene-3,8-diol (56 g, 329 mmole) was treated as described in Example 6 (Step 3) to give diethyl tetradeca-4E,10E-diene-1,14-dioate (46 g, 53% yield). $C_{14}H_{30}O_4$ (262 g/mole). bp: 165° C./0.1 mm Hg. $^1$HNMR (500 MHz, CDCl$_3$): 1.24 (t, 6H), 1.30 (m, 4H), 1.93 (m, 4H), 2.28 (m, 4H), 2.34 (m, 4H), 4.10 (q, 4H), 5.40 (m, 4H) ppm. $^{13}$CNMR (125 MHz, CDCl$_3$): 14.2, 27.9, 28.9, 32.3, 34.4, 60.1, 128.1, 131.6, 173.2 ppm. IR ($v_{max}(cm^{-1})$): 3000(m), 2940(s), 2860 (w), 1740(s), 1450(w), 1380(m), 1250(m), 1180(s), 1020 (m), 970(m). MS (m/z): 265(M-45), 264, 219, 149, 135, 121, 107, 93, 81, 67, 55, 41.

E8-Step 4: Preparation of 14-hydroxycyclotetradeca-4E, 10E-dien-1-one:

Diethyl tetradeca-4E,10E-diene-1,14-dioate (34.68 g, 132 mmole) was treated as described in Example 6 (Step 4) to give 14-hydroxycyclotetradeca-4E,10E-dien-1-one (11.5 g, 46% yield). $C_{14}H_{22}O_2$ (222.33 g/mole). bp: 134° C./0.9 mm Hg. $^1$HNMR (500 MHz, CDCl$_3$): 1.30 (m, 4H), 1.45 (m, 1H), 1.68 (m, 1H), 1.80–2.05 (m, 4H), 2.10 (m, 2H), 2.26 (m, 1H), 2.45 (m, 1H), 2.55 (m, 2H), 3.53 (m, 1 h), 4.18 (m, 1H), 5.18 (m, 1H), 5.40 (m, 3H) ppm. $^{13}$CNMR (125 MHz, CDCl$_3$): 26.1*, 27.0, 27.6, 29.1, 29.2, 32.8, 38.3, 76.8, 128.5, 129.5, 132.2, 133.3, 213.0 ppm. IR ($v_{max}(cm^{-1})$): 3475(bm), 2950(s), 2910(s), 2850(s), 1715(s), 1440(m), 1400(m), 970(s). MS (m/z): 222(M$^+$), 121, 109, 95, 84, 79, 67, 54, 41.

E8-Step 5: Preparation of cyclotetradeca-4E,10E-dien-1-one:

14-Hydroxycyclotetradeca-4E,10E-dien-1-one (1.90 g, 8.55 mmole) was treated as described in Example 6 (Step 5)

to give cyclotetradeca-4E,10E-dien-1-one (1.32 g, 75% yield). $C_{14}H_{22}O$ (206.33 g/mole). bp: 150° C./0.13 mm Hg. $^1$HNMR (500 MHz, $CDCl_3$): 1.36 (m, 6H), 1.66 (m, 2H), 1.89 (m, 2H), 1.92 (m, 2H), 2.03 (m, 2H), 2.26 (m, 2H), 2.40 (m, 4H), 5.16 (m, 1H), 5.38 (m, 3H) ppm. $^{13}$CNMR (125 MHz, $CDCl_3$): 21.2, 26.4, 26.8, 27.9, 30.2, 30.3, 31.4, 41.9, 42.7, 129.4, 129.8, 131.5, 132.0, 211.3 ppm. IR ($v_{max}(cm^{-1})$): 2940(s), 2910(s), 2850(s), 1715(s), 1410(m), 1365(m), 1110(m), 970(s). MS (m/z): 206($M^+$), 163, 149, 138, 123, 109, 95, 79, 67, 55, 41.

EXAMPLE 9

(E9): cyclopentadeca-4E,12E-dien-1-one

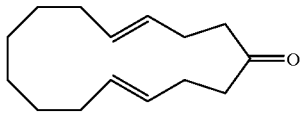

E9-Step 1: Preparation of ethyl 15-oxocyclopentadeca-3E,11E-dienecarboxylate:

To a flask containing a solution of potassium t-butoxide (6.30 g, 61.1 mmole) in toluene (80 ml), heated to reflux, was added slowly (via syringe pump over 15 hours) a solution of diethyl hexadeca-4E,12E-diene-1,16-dioate (4.32 g, 12.8 mmole) in toluene (10 ml). After the addition was complete the mixture was maintained at reflux for an additional 5 hours. The reaction mixture was cooled to room temperature and to the mixture was added acetic acid and then water. To the mixture was then added diethyl ether, the layers separated and the organic layer was dried with sodium sulfate and evaporated to provide the crude ethyl 15-oxocyclopentadeca-3E,11E-dienecarboxylate which was used directly in the next step. $C_{18}H_{28}O_3$ (292.42 g/mole). $^1$HNNR (500 MHz, $CDCl_3$): 1.16 (m, 4H), 1.23 (t, 3H), 1.34 (m, 4H), 1.99 (m, 4h), 2.13 (m, 1H), 2.40 (m, 2H), 2.55 (m, 1H), 2.70 (m, 2H), 3.50 (dd, 1H), 4.13 (q, 2H), 5.40 (m, 4H) ppm. $^{13}$CNMR (125 MHz, $CDCl_3$): 14.1, 26.2, 27.0, 27.4, 27.7, 28.6, 31.0, 31.1, 31.2, 43.6, 58.4, 61.3, 126.3, 129.1, 131.6, 133.6, 169.5, 204.6 ppm. IR ($v_{max}(cm^{-1})$): 2990, 2940, 2910, 2850, 1745, 1720, 1640, 1440, 1370, 1260, 1040, 970, 860. MS (m/z): 292($M^+$), 247, 163, 149, 135, 121, 107, 95, 81, 67, 55, 41.

E9-Step 2: Preparation of cyclopentadeca-4E,12E-dien-1-one:

The crude ethyl 15-oxocyclopentadeca-3E,11E-dienecarboxylate (prepared as described above) was treated with ethanol (10 ml) and 3N aqueous hydrochloric acid (20 ml) and heated to reflux for 20 hours. The solution was cooled and diethyl ether and water were added. The layers were separated and the organic fraction was dried with magnesium sulfate, filtered and evaporated to provide a brown oil which was purified by column chromatography (10% diethyl ether/hexane) to afford cyclopentadeca-4E,12E-dien-1-one (0.50 g, 17% yield from diethyl hexadeca-4E,12E-diene-1,16-dioate). $C_{15}H_{24}O$ (220.36 g/mole). $^1$HNMR (500 MHz, $CDCl_3$): 1.15 (m, 4H), 1.34 (m, 4H). 1.97 (m, 4H), 2.24 (m, 4H), 2.45 (m, 4H), 5.30 (m, 2H), 5.39 (m, 2H) ppm. $^{13}$CNMR (125 MHz, $CDCl_3$): 26.7, 27.4, 28.4, 31.2, 42.8, 129.2, 131.3, 210.4 ppm. IR ($v_{max}(cm^{-1})$): 2990, 2950, 2910, 2850, 1720, 1440, 1400, 1360, 1080, 980, 720. MS (m/z): 220($M^+$), 177, 163, 149, 135, 121, 109, 95, 81, 67, 55, 41.

EXAMPLE 10

(E10): 3,14-dimethylcyclohexadeca-4E,12E-dien-1-one

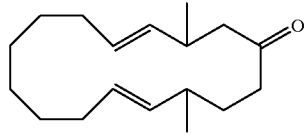

E10-Step 1: Preparation of tetradeca-2E,12E-diene-4,11-diol:

Preparation of the di-Grignard reagent from 1,6-dibromohexane (61 g, 250 mmole) and treatment with trans-crotonaldehyde (38.5 g, 550 mmole), as described in Example 6 (Step 2/Method A), gave tetradeca-2E,12E-diene-4,11-diol (46 g, 56% yield). $C_{14}H_{26}O_2$ (226.36 g/mole). mp 63–64° C., colorless cubes (recrystallized from ethyl acetate). $^1$HNMR (500 MHz, $CDCl_3$): 1.56–1.20 (m, 12H), 1.594 (brs, 2H), 1.674 (d, 6H), 3.995 (dt, 2H), 5.48–5.40 (m, 2H), 5.66–5.58 (m, 2H) ppm. $^{13}$CNMR (125 MHz, $CDCl_3$): 17.70, 25.47, 29.57, 37.33, 73.18, 126.76, 134.46 ppm. IR ($v_{max}(cm^{-1})$): 3312(s), 3229(s), 2928(s), 2908(s), 2847(s), 1493(m), 1462(m), 1440(m), 1143(s), 1118(m), 1078(m), 1006(w), 960(s), 918(w), 877(m), 787 (w). MS (m/z): 208(M-18), 190, 175, 161, 147, 138, 122, 109, 95, 81, 71, 55, 41.

E10-Step 2: Preparation of dimethyl3,14-dimethylhexadeca-4E,12E-diene-1,16-dioate:

A mixture of tetradeca-2E,12E-diene-4,11-diol (5.0 g, 22.0 mmole), trimethyl orthoacetate (20 ml, 165 mmole), and t-butylacetic acid (0.1 g, 0.86 mmole) was heated to 120–140° C. for 3.0 hours with the slow distillation of the methanol formed during the reaction. The solution was cooled to 80° C. and the lower boiling materials were removed by vacuum distillation to afford dimethyl 3,14-dimethylhexadeca-4E,12E-diene-1,16-dioate (5.59 g, 75% yield) as an oil which was suitable for use in the subsequent reaction. $C_{20}H_{34}O_4$ (338.49 g/mole). $^1$HNMR (500 MHz, $CDCl_3$): 1.001 (d, 6H), 1.33–1.18 (m, 8H), 1.929 (dd, 4H), 2.257 (dt, 4H), 2.599 (dt, 2H), 3.634 (s, 6H), 5.32–5.27 (m, 2H), 5.43–5.36 (m, 2H) ppm. $^{13}$CNMR (125 MHz, $CDCl_3$): 20.54, 28.99, 29.51, 32.52, 33.76, 41.89, 51.49, 129.74, 134.10, 173.22 ppm. IR ($v_{max}(cm^{-1})$): 2926(s), 2912(s), 2852(m), 1742(s), 1458(m), 1437(m), 1358(m), 1284(m), 1246(m), 1192(m), 1168(m), 1072(w), 1008(m), 970(m), 879(w), 839(w), 725(w). MS (m/z): 338($M^+$), 306, 275, 264, 257, 246, 233, 223, 215, 204, 191, 177, 163, 149, 135, 121, 108, 95, 81, 67, 55, 41.

E10-Step 3: Preparation of 16-hydroxy-3,14-dimethylcyclohexadeca-4E,12E-dien-1-one:

Dimethyl 3,14-dimethylhexadeca-4E,12E-diene-1,16-dioate (5.0 g, 14.8 mmole) was treated as described in Example 6 (Step 4) to give 16-hydroxy-3,14-dimethylcyclohexadeca-4E,12E-dien-1-one (3.29 g, 80% yield) as an isomeric mixture which was used directly in the next step. For analytical purposes this isomeric mixture can be separated into two fractions by flash chromatography. Fraction A: $^1$HNMR (500 MHz, $CDCl_3$): 0.996(d, 3H), 1.078(d, 3H), 1.61–1.03(m, 11H), 2.05–1.93 (m, 3H), 2.22–2.13(m, 1H), 2.358(dd, 4H), 2.54–2.42(m, 1H), 2.67–2.58(m, 1H), 3.361(d, 1H), 4.13–4.08(m, 1H), 5.21–5.11(m, 2H), 5.52–5.40(m, 2H) ppm. $^{13}$CNMR (125 MHz, $CDCl_3$): 21.36, 22.18, 26.94, 27.67, 27.79, 28.66, 28.22, 28.72, 29.38, 30.89, 30.94, 31.17, 34.78, 34.92, 40.39, 41.11, 45.17, 45.58, 75.58, 75.84, 77.00, 77.25, 133.4–131.3(m), 135.3–134.0(m), 213.57 ppm (contains isomers). IR ($v_{max}$(cm$^{-1}$)): 3481 (m), 2930(s), 2911 (s), 2859(s), 2361 (w), 2340(w), 1707(s), 1456(m), 1377(w), 1354(w), 1279(w), 1250(w), 1090(m), 1049(w), 972(s), 856(w), 721(w), 596(w). MS (m/z): 278(M$^+$), 260, 249, 235, 217, 205, 161, 149, 135, 121, 109, 95, 81, 67, 55, 41. Fraction B: $^1$HNMR (500 MHz, CDCl$_3$): 0.996 (d, 3H), 1.017(d), 3H), 1.33–1.10(m, 8H), 1.47–1.38(m, 1H), 1.68–1.60(m, 1H), 1.96–1.87(m, 4H), 2.257(dd, 1H), 2.38–2.28(m, 1H), 2.528(dd, 4H), 2.81–2.71(m, 1H), 3.463 (d, 1H), 4.13–4.09(m, 1H), 5.44–5.30 m, 4H) ppm. $^{13}$CNMR (125 MHz, CDCl$_3$): 27.65, 27.99, 28.09, 28.28, 28.35, 29.04, 31.54, 31.78, 31.85, 31.92, 32.13, 32.64, 34.24, 40.27, 41.06, 41.13, 46.14, 75.17, 75.41, 75.76, 79.01, 129.5–128.9(m), 130.6–129.6(m), 134.2–133.6(m), 136.7–136.1(m), 211.99, 213.22 ppm (contains isomers). IR ($v_{max}$(cm$^{-1}$)): 3482(m), 2930(s), 2913(s), 2857(s), 2359(w), 2342(w), 1711(s), 1456(m), 1375(w), 1280(w), 1084(w), 1040(w), 972(s), 717(w). MS (m/z): 278(M$^+$), 260, 249, 235, 217, 205, 161, 149, 135, 121, 109, 95, 81, 67, 55, 41.

E10-Step 4: Preparation of 3,14dimethylcyclohexadeca-4E,12E-dien-1-one:

16-Hydroxy-3,14-dimethylcyclohexadeca4E,12E-dien-1-one(2.39g, 8.58 mmole) was treated as described in Example 6 (Step 5) to give 3,14-dimethylcyclohexadeca4E,12E-dien-1-one (1.79 g, 80% yield). C$_{18}$H$_{30}$O (262.43 g/mole). $^1$HNMR (500 MHz, CDCl$_3$): 0.964 (dd, 3H), 1.011 (d, 3H), 1.48–1.07 (m, 10H), 1.73–1.53 (m, 1H), 2.07–1.90 (m, 4H), 2.45–2.24 (m, 4H), 2.72–2.57 (m, 1H), 5.20–5.09 (m, 1H), 5.40–5.24 (m, 3H) ppm. $^{13}$CNMR (125 MHz, CDCl$_3$): 20.75, 21.35, 27.5–26.7(m), 28.23, 28.57, 30.71, 31.11, 31.47, 33.17, 36.00, 41.03, 51.01, 130.7–128.9(m), 134.7–133.8(m), 136.0–135.0(m), 211.41 ppm. IR ($v_{max}$(cm$^{-1}$)): 2953(s sh), 2932(s), 2908(s), 2856(s), 1712(s), 1456(m), 1408(w), 1371(m), 1275(w), 1147(w), 1107(w), 1049(w), 972(s), 860(w), 723(w). MS (m/z): 262(M$^+$), 247, 233, 219, 205, 191, 177, 163, 149, 135, 121, 109, 95, 81, 67, 55, 41.

EXAMPLE 11

(E11): 3,13-dimethylcyclopentadeca-4E,11E-dien-1-one

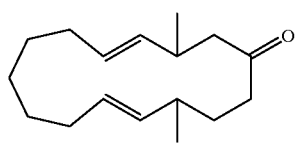

E11-Step 1: Preparation of trideca-2E,11E-diene-4,10-diol:

Preparation of the di-Grignard reagent from 1,5-dibromopentane (57.5 g, 250 mmole) and treatment with trans-crotonaldehyde (37.0 g, 528 mmole), as described in Example 6 (Step 2/Method A), gave trideca-2E,11E-diene-4,10-diol (23.3 g, 44% yield). C$_{13}$H$_{24}$O$_2$ (212.33 g/mole). mp 62–63° C., colorless plates (recrystallized from ethyl acetate). $^1$HNMR (500 MHz, CDCl$_3$): 1.56–1.20 (m, 10H), 1.72–1.59 (brs, 2H), 1.666 (d, 6H), 3.986 (dt, 2H), 5.47–5.41 (m, 2H), 5.65–5.57 (m, 2H) ppm. $^{13}$CNMR (125 MHz, CDCl$_3$): 17.70, 25.47, 29.52, 37.27, 73.11, 126.69, 134.47 ppm. IR ($v_{max}$(cm$^{-1}$)): 3308(s), 3223(s), 2962(m), 2928(s), 2908(s), 2852(s), 1496(m), 1460(m), 1435(m), 1292(w), 1223(w), 1142(s), 1060(s), 1022(m), 1008(w), 960(s), 935 (m), 885(m), 812(m), 704(w), 650(w).

E11-Step 2: Preparation of dimethyl 3,13-dimethylpentadeca-4E,11E-diene-1,15-dioate:

Treatment of trideca-2E,11E-diene-4,10-diol (5.0 g, 23.5 mmole) as described in Example 10 (Step 2) gave dimethyl 3,13-dimethylpentadeca-4E,11E-diene-1,15-dioate (6.0 g, 79% yield). C$_{19}$H$_{32}$O$_4$ (324.46 g/mol). $^1$HNMR (500 MHz, CDCl$_3$): 0.985 (d, 6H), 1.32–1.18 (m, 6H), 1.915 (dd, 4H), 2.240 (dt, 4H), 2.583 (dt, 2H), 3.616 (s, 6H), 5.31–5.25 (m, 2H), 5.41–5.34 (m, 2H) ppm. $^{13}$CNMR (125 MHz, CDCl$_3$): 20.49, 28.58, 29.39, 32.46, 33.73, 41.86, 51.46, 129.67, 133.91, 173.17 ppm. IR ($v_{max}$(cm$^{-1}$)): 2995(s), 2930(s), 2854(s), 1739(s), 1456(m), 1437(s), 1358(m), 1284(m), 1224(m), 1244(m), 1192(w), 1168(m), 1072(w), 1008(m), 970(s), 879(w), 839(w), 727(w), 638(w). MS (m/z): 324 (M$^+$), 306, 292, 261, 250, 243, 232, 219, 210, 201, 191, 177, 163, 149, 135, 121, 108, 95, 81, 67, 55, 41.

E11-Step 3: Preparation of 15-hydroxy-3,13-dimethylcyclopentadeca-4E,11E-dien-1-one:

Dimethyl 3,13-dimethylpentadeca-4E,11E-diene-1,15-dioate (5.5 g, 17 mmole) was treated as described in Example 6 (Step 4) to give 15-hydroxy-3,13-dimethylcyclopentadeca-4E,11E-dien-1-one (1.89 g, 42% yield) as an isomeric mixture which was used directly in the next step. For analytical purposes this isomeric mixture can be separated into two fractions by flash chromatography. Fraction A: $^1$HNMR (500 MHz, CDCl$_3$): 1.032(d, 3H), 1.046(d, 3H), 1.18–1.07(m, 1H), 1.45–1.18(m, 6H), 1.747 (ddd, 1H), 1.96–1.83 (m, 2H), 2.10–1.96(m, 2H), 2.294(dd, 1H), 2.441(dt, 1H), 2.570(dd, 1H), 2–78–2.67(m, 1H), 3.333 (d, 1H), 4.14–4.09(m, 1H), 5.40–5.18(m, 4H) ppm. $^{13}$CNMR (125 MHz, CDCl$_3$): 19.98, 21.35, 27.67, 27.72, 28.05, 32.24, 32.45, 32.60, 33.76, 41.25, 45.98, 75.33, 75.52, 130.7–129.9(m), 134.64, 134.89, 136.3–135.7(m), 213.32 (contains isomers). IR ($v_{max}$(cm$^{-1}$)): 3389(m), 2924 (s), 2913(s), 2852(s), 1712(s), 1456(m), 1435(w), 1412(w), 1377(w), 1350(w), 1275(w), 1090(m), 1028(m), 970(s), 815(w), 733(w), 625(w). MS (m/z): 264(M$^+$), 221, 203, 191, 163, 149, 135, 121, 109, 95, 81, 67, 55, 41. Fraction B: $^1$HNMR (500 MHz, CDCl$_3$): 1.002(d, 3H), 1.078(d, 3H), 1.57–0.90(m, 8H), 2.05–1.83(m, 3H), 2.26–2.12(m, 2H), 2.57–2.44(m, 3H), 3.485(d, 1H), 4.16–4.10(m, 1H), 5.100 (ddd, 1H), 5.32–5.18(m, 2H), 5.43(ddd, 4H) ppm. $^{13}$CNMR (125 MHz, CDCl$_3$): 21.71, 22.01, 22.43, 27.28, 27.72, 28.20, 28.63, 29.19, 32.15, 32.38, 34.50, 34.60, 36.34, 40.43, 42.05, 45.53, 45.64, 76.55, 76.73, 130.0–129.4(m), 132.9–131.1(m), 135.4–134.5(m), 213.18, 214.21 (contains isomers). IR ($v_{max}$(cm$^{-1}$)): 3482(m), 2928(s), 2915(s), 2854 (s), 1705(s), 1456(m), 1395(w), 1335(w), 1281 (m), 1231(w), 1094(m), 972(s), 856(w), 729(w), 610(w). MS (m/z): 264(M$^+$), 221, 203, 191, 163, 149, 135, 121, 109, 95, 81, 67, 55, 41.

EXAMPLE 11

Step 4: Preparation of 3,13-dimethylcyclopentadeca4E,11E-dien-1-one

15-Hydroxy-3,13-dimethylcyclopentadeca-4E,11E-dien-1-one (1.69 g, 6.4 mmole) was treated as described in Example 6 (Step 5) to give 3,13-dimethylcyclopentadeca-4E,11E-dien-1-one (1.28 g, 81% yield).C$_{15}$H$_{24}$O (220.36 g/mole). $^1$HNMR (500 MHz, CDCl$_3$): 1.15 (m, 2H), 1.22–1.39 (m, 5H), 1.63 (m, 2H), 2.0 (m, 6H), 2.29 (m, 2H), 2.41 (m, 3H), 5.25 (m, 2H), 5.34 (m, 2H) ppm. $^{13}$CNMR (125 MHz, CDCl$_3$): 21.8, 26.5, 28.0, 28.1*, 30.7, 31.9, 32.0, 42.5, 42.9, 129.2, 130.3, 132.2, 132.3, 212.5 ppm. IR ($v_{max}$(cm$^{-1}$)): 2950(s), 2920(s), 2860(s), 1715(s), 1440(m), 1370(m), 970(s). MS (m/z): 220(M$^+$), 202, 191, 177, 152, 135, 123, 109, 95, 79, 67, 55, 41.

EXAMPLE 12

(E12): 8-methylcyclopentadeca4E,11E-dien-1-one

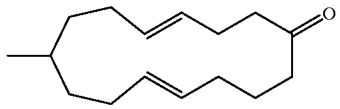

E12-Step 1: Preparation of 6-methylundeca-1,10-diene-3,9-diol:

Preparation of the di-Grignard reagent from 1,5-dibromo-3-methylpentane (46 g, 189 mmole) and treatment with acrolein (23.3 g, 415 mmole), as described in Example 6 (Step 2/Method A), gave 6-methylundeca-1,10-diene-3,9-diol (29.2 g, 78% yield). $C_{12}H_{22}O_2$ (198.31 g/mole). bp: 115° C., 0.4 mm Hg. $^1$HNMR (500 MHz, $CDCl_3$): 0.86 (d, 3H), 1.08–1.58 (m, 9H), 1.95 (bs, 2H), 4.02 (m, 2H), 5.06 (d, 2H), 5.18 (m, 2H), 5.79–5.87 (m, 2H) ppm. $^{13}$CNMR (125 MHz, $CDCl_3$): 19.66, 32.38, 32.66, 32.77, 34.47, 73.50, 73.67, 114.62, 114.70, 141.32, 141.38. IR ($v_{max}(cm^{-1})$): 3360(bs), 3080(w), 2925(s), 2860(s), 1645(w), 1430(w), 995(s), 920(s). MS (m/z): 165(M-33), 151, 147, 109, 95, 81, 67, 57, 41.

E12-Step 2: Preparation of diethyl 8-methylpentadeca-4E,11E-diene-1,15-dioate:

6-Methylundeca-1,10-diene-3,9-diol (29.2 g, 148 mmole) was treated as described in Example 6 (Step 3) to give diethyl 8-methylpentadeca-4E,11E-diene-1,15-dioate (30 g, 60% yield). $C_{20}H_{34}O_4$ (338.49 g/mol). $^1$HNMR (500 MHz, $CDCl_3$): 0.83 (d, 3H), 1.03–1.40 (m, 5H), 1.24 (t, 6H), 1.89–2.08 (m, 4H), 2.28–2.37 (m, 8H), 4.10 (q, 4H), 5.35–5.50 (m, 4H) ppm. $^{13}$CNMR (125 MHz, $CDCl_3$): 14.38, 19.42, 28.03, 30.06, 31.87, 34.51, 36.83, 60.31, 127.85, 132.00, 173.36 ppm. IR ($v_{max}(cm^{-1})$): 2965(w), 2925(s), 2850(w), 1740(s), 1460(w), 1375(w), 1160(w), 1040(w), 970(w). MS (m/z): 338(M$^+$), 292, 247, 163, 149, 135, 121, 109, 95, 81, 67, 55, 41.

E12-Step 3: Preparation of 15-hydroxy-8-methylcyclopentadeca-4E,11E-dien-1-one:

Diethyl 8-methylpentadeca-4E,11E-diene-1,15-dioate (10.6 g, 31.4 mmole) was treated as described in Example 6 (Step 4) to give 15-hydroxy-8-methylcyclopentadeca-4E,11E-dien-1-one (4.0 g, 51% yield). $C_{16}H_{26}O_2$ (250.38 g/mole). $^1$HNMR (500 MHz, $CDCl_3$): (mixture of diastereomers) 0.79–0.83 (2d, 3H), 1.10–1.50 (m, 8H), 1.81–2.6 (m, 11H), 3.37–3.43 (2d, 1H), 4.10–4.16 (m, 1H), 5.3–5.5 (m, 4H) ppm. $^{13}$CNMR (125 MHz, $CDCl_3$): (mixture of diastereomers) 18.82, 19.33, 27.41, 27.67, 27.75, 28.12, 28.67, 28.95, 28.99, 29.10, 29.30, 29.72, 32.41, 32.43, 35.22, 35.71, 35.89, 36.10, 37.90, 38.17, 128.36, 128.39, 128.50, 128.51, 132.70, 132.96, 133.43, 133.97, 214.04, 214.40 ppm. IR ($v_{max}(cm^{-1})$): 3435(bs), 2930(s), 2850(s), 1715(s), 1445(m), 1380(w), 1250(w), 975 (m), 860(w). MS (m/z): (diastereomer 1); 250(M$^+$), 232, 221, 203, 177, 163, 149, 135, 121, 109, 95, 81, 67, 55, 41. (diastereomer2); 250(M$^+$), 232, 221, 203, 177, 163, 149, 135, 121, 109, 95, 81, 67, 55, 41.

EXAMPLE 12

Step 4: Preparation of 8-methylcyclopentadeca-4E,11E-dien-1-one

The crude product obtained in the previous step was subjected to flash column chromatography to provide 8-methylcyclopentadeca-4E,11E-dien-1-one (0.30 g, 4% yield from diethyl 8-methylpentadeca-4E,11E-diene-1,15-dioate). $C_{16}H_{26}O$ (234.38 g/mol). $^1$HNMR (500 MHz, $CDCl_3$): 0.76 (d, 3H), 1.10–1.45 (m, 7H), 1.65–1.73 (m, 1H), 1.98–2.12 (m, 6H), 2.23–2.43 (m, 5H), 5.25 (m, 2H), 5.35 (m, 2H) ppm. $^{13}$CNMR (125 MHz, $CDCl_3$): 18.39, 21.76, 26.99, 27.83, 29.04, 29.18, 30.67, 35.81, 35.86, 42.08, 42.50, 129.09, 129.83, 131.96, 131.99, 212.41 ppm. IR ($v_{max}(cm^{-1})$): 2950(s), 2920(s), 2850(s), 1715(s), 1450 (m), 1380(w), 975(s). MS (m/z): 234(M$^+$), 219, 201, 191, 166, 149, 135, 123, 109, 95, 81, 67, 55, 41.

EXAMPLE 13

(E13): 2-methylcyclopentadeca-4E,12E-dien-1-one

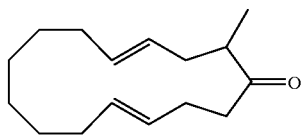

E13-Step 1: Preparation of ethyl 1-methyl-15-oxocyclopentadeca-3E,11E-dienecarboxylate:

Into a flask containing a solution of crude ethyl 15-oxocyclopentadeca-3E,11E-dienecarboxylate (0.280 g, 0.96 mmole) intoluene (3 ml) was added 60% sodium hydride dispersion in mineral oil (0.026 g, 1.06 mmole). The mixture was stirred at room temperature for an additional 24 hours. To the mixture was added 10% aqueous hydrochloric acid, the mixture was shaken, the layers separated, and the organic layer was dried over anhydrous magnesium sulfate, filtered and evaporated to give ethyl 1-methyl-15-oxocyclopentadeca-3E,11E-dienecarboxylate (0.180 g, 61% yield). $C_{19}H_{30}O_3$ (306 g/mol): $^1$HNMR (500 MHz, $CDCl_3$): 1.10–1.20 (m, 4H), 1.23 (t, 3H), 1.32 (s, 3H), 1.33–1.40 (m, 3H), 1.92–2.30 (m, 5H), 2.20 (m, 1H), 2.30 (m, 2H), 2.55 (m, 2H), 2.76 (dd, 1H), 4.15 (q, 2H), 5.28 (m, 1H), 5.40 (m, 3H) ppm. $^{13}$CNMR (125 MHz, $CDCl_3$): 14.02, 19.60, 26.21, 26.87, 26.96, 28.01, 30.69, 31.00, 38.13, 38.79, 58.76, 61.19, 124.70, 129.33, 131.86, 134.12, 173.39, 207.00 ppm. IR ($v_{max}(cm^{-1})$): 2980(s), 2920(s), 2850(s), 1740(s), 1720 (s), 1645(m), 1445(m), 1260(w), 1040(w), 970(s).

E13-Step 2: Preparation of 2-methylcyclopentadeca-4E,12E-diene-1-one:

A solution of ethyl 1-methyl-15-oxocyclopentadeca-3E,11E-dienecarboxylate (0.180 g, 0.59 mmole) and potassium hydroxide (0.15 g, 2.68 mmole) in 50% aqueous ethanol (3 ml) was heated to 65° C. for 5 hours. The solvents were removed by reduced pressure distillation and to the residue was added 5% aqueous hydrochloric acid and methylene chloride. The mixture was shaken, the layers separated, and the organic layer was dried over anhydrous magnesium sulfate, filtered and evaporated to give the crude product. The crude product was purified by flash chromatography to give 2-methylcyclopentadeca-4E,12E-diene-1-one (0.060 g, 44% yield). $C_{16}H_{26}O$ (234 g/mol): $^1$HNMR (500 MHz, $CDCl_3$): 1.05 (d, 3H), 1.17 (m, 3H), 1.25–1.41 (m, 3H), 1.97 (m, 4H), 2.08 (m, 2H), 2.27 (m, 1H), 2.36 (m, 1H), 2.46 (m, 1H), 2.52 (m, 1H), 2.59 (m, 1H), 5.32 (m, 3H), 5.46 (m, 1H) ppm. $^{13}$CNMR (125 MHz, $CDCl_3$): 17.59, 26.07, 26.72, 27.19, 27.65, 28.74, 30.76, 30.98, 36.59, 42.32, 46.34, 127.81, 129.61, 131.06, 132.12, 213.70 ppm. IR ($v_{max}(cm^{-1})$): 3030(w), 2920(s), 2852(s), 1714(s), 1456(m), 1436(m), 970(s). MS (m/z): 234(M), 219, 191, 177, 163, 149, 135, 121, 109, 95, 81, 67, 55, 41.

EXAMPLE 14

(E14): Preparation of 3,14-dimethylcyclohexadecan-1-one

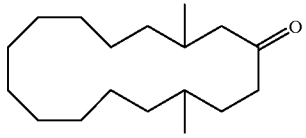

E14: Hydrogenation of 3,14dimethylcyclohexadeca-4E,12E-dien-one

A Parr bottle was charged with 3,14-dimethylcyclohexadeca-4E,12E-dien-one (0.203 g, 0.77 mmole), ethyl acetate (36 ml), ethanol (4 ml) and 5% palladium-on-carbon (0.050 g). The vessel was pressurized to 43 psi with hydrogen gas and the solution was shaken vigorously for 2 hours. The pressure was brought down to atmospheric pressure and the reaction mixture was filtered through a pad of Celite and the solvents were removed by distillation under reduced pressure to afford 3,14-dimethylcyclohexadecan-1-one (0.206 g, 100% yield). $C_{18}H_{34}O$ (266.47 g/mole). $^1$HNMR (500 MHz, CDCl$_3$): 0.861 (dd, 3H), 0.909 (dd, 3H), 1.38–1.03 (m, 20H), 1.62–1.38 (m, 3H), 2.10–1.98 (m, 1H), 2.18–2.11 (m, 1H), 2.43–2.33 (m, 3H) ppm. $^{13}$CNMR (125 MHz, CDCl$_3$): 20.44, 20.80, 24.15, 25.21, 26.47, 26.50, 26.76, 27.06, 27.47, 29.10, 29.45, 31.31, 34.50, 35.61, 40.24, 50.48, 211.86 ppm. IR ($\nu_{max}$(cm$^{-1}$)): 2930(s), 2910(s), 2856(s), 1713(s), 1460(s), 1412(w), 1375(m), 1146(w), 1096(w), 1059(w). MS (m/z): 266(M$^+$), 251, 237, 223, 208, 152, 139, 125, 109, 97, 85, 69, 55, 41.

EXAMPLE 15

(E15): Cyclopentadecanone (exaltone)

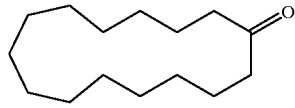

E15: Hydrogenation of cyclopentadeca-4E,12E-dien-1-one:

A flask was charged with cyclopentadeca-4E,12E-dien-1-one (0.10 g, 0.45 mmole), ethanol (5 ml) and 5% palladium-on-carbon (0.01 g). The mixture was stirred at room temperature under 1 atm of hydrogen gas for 1 hour. The reaction mixture was filtered through celite and concentrated to provide cyclopentadecanone (exaltone) (0.09 g, 88% yield). $C_{15}H_{28}O$ (224.39 g/mole). $^1$HNMR (500 MHz, CDCl$_3$): 1.25 (m, 20H), 1.60 (m, 4H), 2.35 (t, 4H) ppm. $^{13}$CNMR (125 MHz, CDCl$_3$): 23.40, 26.25, 26.39, 26.69, 26.74, 27.54, 42.05, 212.50, ppm. IR ($\nu_{max}$(cm$^{-1}$)): 2924(s), 2854(s), 1708(s), 1458(m).

EXAMPLE 16

(E16): Cyclopentadec-4E-en-1-one

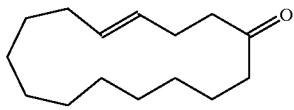

E16: Partial hydrogenation of cyclopentadeca-4E,12E-dien-1-one:

A flask was charged with cyclopentadeca-4E,12E-dien-1-one (0.10 g, 0.45 mmole), ethanol (5 ml) and 5% palladium-on-carbon (0.010 g). The mixture was stirred at room temperature under 1 atm of hydrogen gas for 30 minutes. The reaction mixture was filtered through celite and concentrated to provide crude cyclopentadec-4E-en-1-one (0.09 g, 88% yield). $C_{15}H_{30}O$ (226.41 g/mole). $^{13}$CNMR (125 MHz, CDCl$_3$): 21.65, 21.72, 25.85, 26.12, 27.86, 30.57, 31.02, 31.74, 31.82, 42.30, 42.49, 130.08, 132.00, 210.00 ppm. GC analysis indicates product to be a mixture of cyclopentadec-4E-en-1-one (39%), cyclopentadeca-4E,12E-dien-1-one (37%), and cyclopentadecanone (24%).

The foregoing compounds possess a useful fragrance quality having utility in the fragrance industry. The odor qualities of the materials were evaluated by an expert panel of perfimers (approximately 25 individuals). Samples of the materials to be evaluated were applied, either neat or in solution, to chemically pure perfume blotters and were assessed for standard odor characteristics. The results of the assessments are shown below. Table 1 illustrates the odor characteristics of Examples 6–13.

TABLE 1

| Example | Name | Odor Characteristics |
| --- | --- | --- |
| Example 6 | cyclohexadeca-4E,12E-dien-1-one | musky, amber, woody |
| Example 7 | cyclopentadeca-4E,11E-dien-1-one | musky, woody |
| Example 8 | cyclotetradeca-4E,10E-dien-1-one | woody, lactonic, musky, floral |
| Example 9 | cyclopentadeca-4E,12E-dien-1-one | woody, musky |
| Example 10 | 3,14-dimethylcyclohexadeca-4E,12E-dien-1-one | slightly fruity woody, musky on skin |
| Example 11 | 3,13-dimethylcyclopentadeca-4E,11E-dien-1-one | slightly fruity woody, musky on skin |
| Example 12 | 8-methylcyclopentadeca-4E,11E-dien-1-one | oily, like linseed |
| Example 13 | 2-methylcyclopentadeca-4E,12E-dien-1-one | weak, lightly woody |

The compounds of the invention may be used alone, or in combination with carriers, additional perfumery materials, and/or other ingredients known to those of ordinary skill in the art, to provide various products, such as perfumes, colognes, soaps and cosmetics. Table 2 illustrates the use of Example 8 in a fragrance composition.

TABLE 2

| GL-FLOR-116 (Fragrance using Example 8) | | |
| --- | --- | --- |
| Name | Formula Parts | Weight % |
| cyclotetradeca-4E,10E-dien-1-one (Example 8) | 80.0 | 11.43 |
| Ambroxan @ 10% DPG | 0.5 | 0.07 |
| Amyl salicylate | 30.0 | 4.28 |
| Courmarin | 10.0 | 1.43 |

TABLE 2-continued

GL-FLOR-116 (Fragrance using Example 8)

| Name | Formula Parts | Weight % |
|---|---|---|
| DH myrcenol | 110.0 | 15.71 |
| Hedione | 20.0 | 2.86 |
| Indole crystal @ 10% DPG | 2.0 | 0.29 |
| Isobutyl quinoline @ 1% DPG | 2.5 | 0.36 |
| Orbitone | 200.0 | 28.57 |
| Kovanol | 45.0 | 6.43 |
| Violet tone FA012 | 60.0 | 8.57 |
| Musk T | 50.00 | 7.14 |
| Oakmoss #1 @ 10% DPG | 10.0 | 1.43 |
| Patchouly oil | 10.0 | 1.43 |
| Santalex T | 20.0 | 2.86 |
| Woodyflor | 50.0 | 7.14 |
| Total: | 700.00 | 100.0 |

The foregoing processes for making macrocyclic diene ketones involve a series of individual reaction steps including Grignard reaction, Claisen rearrangement, acyloin condensation and Dieckman cyclization that are well known to one skilled in the art. However, it is the sequence in which they are employed, coupled with the unique nature of the substrate materials upon which they act, that comprises the novel processes of the present invention.

Having described preferred embodiments of the invention it is to be understood that the invention is not limited to those precise embodiments, and that various changes and modifications may be effected therein by one skilled in the art without departing from the scope or spirit of the invention as defined in the appended claims.

What is claimed is:

1. A compound of the formula (I):

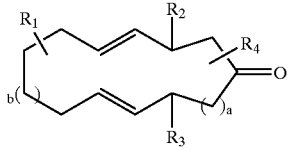

(I)

wherein $R_1$, $R_2$, $R_3$ and $R_4$ are independently a hydrogen atom or a $C_1$ to $C_4$ alkyl, a is the integer 1 or 2, and b is an integer in a range from 1 to 6.

2. A compound according to claim 1, wherein a is the integer 1 or 2 and b is an integer in a range from 2 to 5.

3. A compound according to claim 1, wherein $R_1$, $R_2$, $R_3$, and $R_4$ are independently H or $CH_3$.

4. A method for synthesizing macrocyclic diene ketones of claim 1 comprising:

reacting an optionally substituted 1,ω-dialdehyde with a Grignard reagent to form a bis-allyl alcohol of the following general formula (II):

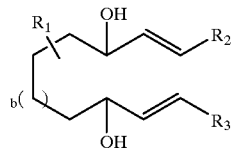

(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

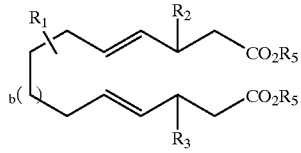

(III)

wherein b is an integer in a range from 1 to 6 and $R_1$, $R_2$ and $R_3$ are each independently a hydrogen atom or a $C_1$ to $C_4$ alkyl, and $R_5$ is the alkyl group of said trialkylorthoacetate;

performing an acyloin condensation of said linear bis-ester to form an α-hydroxyketone; and reducing said α-hydroxyketone to form said macrocyclic diene ketone.

5. A method for synthesizing macrocyclic diene ketones of claim 1 comprising:

reacting an optionally substituted 1,ω-dialdehyde with a Grignard reagent to form a bis-allyl alcohol of the following general formula (II):

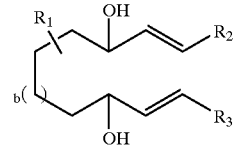

(II)

wherein b is an integer in a range from 1 to 6 and $R_1$ $R_2$ and $R_3$ are independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

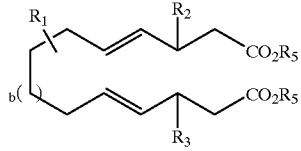

(III)

wherein b is an integer in a range from 1 to 6, $R_1$ $R_2$ and $R_3$ are independently a hydrogen atom or a $C_1$ to $C_4$ alkyl, and $R_5$ is the alkyl group of said trialkylorthoacetate;

reacting said linear bis-ester via a Dieckman cyclization pathway to form a β-ketoester; and hydrolyzing and decarboxylating said β-ketoester to form said macrocyclic diene ketone.

6. The method of claim 5, further comprising:

alkylating said β-ketoester prior to said hydrolyzing and decarboxylating step.

7. A method for synthesizing macrocyclic diene ketones of claim 1 comprising:

reacting a 1,ω-di-Grignard reagent with an unsaturated aldehyde to form a bis-allyl alcohol of the following general formula (II):

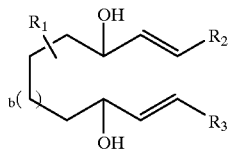

(II)

wherein b is an integer in a range from 1 to 6 and $R_1$, $R_2$, and $R_3$ are each independently a hydrogen atom or a $C_1$ to $C_4$ alkyl;

reacting said bis-allyl alcohol with a trialkylorthoacetate in the presence of acid catalysis resulting in bis-Claisen rearrangement to form a linear bis-ester of the following general formula (III):

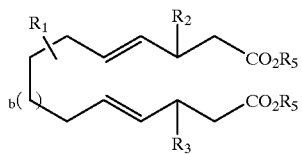

(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

performing an acyloin condensation of said linear bis-ester to form an α-hydroxyketone; and reducing said α-hydroxyketone to form said macrocyclic diene ketone.

8. A method for synthesizing macrocyclic diene ketones of claim 1 comprising:

reacting a 1,ω-di-Grignard reagent with an unsaturated aldehyde to form a bis-allyl alcohol of the following general formula (II):

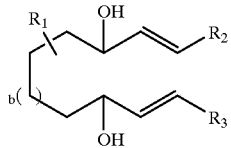

(II)

wherein b is an integer in a range from 1 to 6 and $R_1$, $R_2$, and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

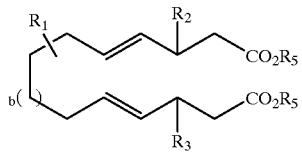

(III)

wherein b is an integer in a range from 1 to 6, $R_1$, $R_2$, and $R_3$ are each independently a hydrogen atom or a $C_1$ to $C_4$ alkyl and $R_5$ is the alkyl group of said trialkylorthoacetate;

reacting said linear bis-ester via a Dieckmann cyclization pathway to form a β-ketoester; and hydrolyzing and decarboxylating said β-ketoester to form said macrocyclic diene ketone.

9. The method of claim 8 further comprising:

alkylating said β-ketoester prior to said hydrolyzing and decarboxylating step.

10. A method for synthesizing saturated or mono-unsaturated macrocyclic ketones having the general formula (IV):

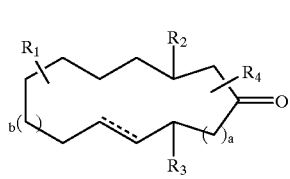

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting an optionally substituted 1,ω-dialdehyde with a Grignard reagent to form a bis-allyl alcohol of the following general formula (II):

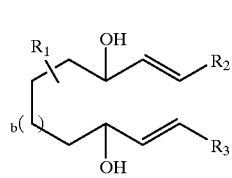

(II)

wherein b is an integer in a range from 1 to 6 and $R_1$, $R_2$, $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

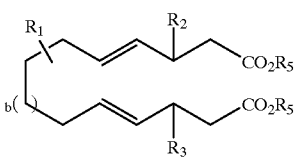

(III)

wherein b is an integer in a range from 1 to 6, $R_1$, $R_2$, $R_3$ are each independently a hydrogen atom or a $C_1$ to $C_4$ alkyl and $R_5$ is the alkyl group of said trialkylorthoacetate;

hydrogenating said linear bis ester to form a saturated or mono-unsaturated linear bis-ester;

performing an acyloin condensation of said saturated or mono-unsaturated linear bis-ester to form an α-hydroxyketone; and reducing said α-hydroxyketone to form said saturated or mono-unsaturated macrocyclic ketone.

11. A method for synthesizing saturated or mono-unsaturated macrocyclic ketones having the following general formula (IV):

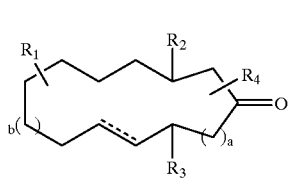

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting an optionally substituted 1,ω-dialdehyde with a Grignard reagent to form a bis-allyl alcohol of the following general formula (II):

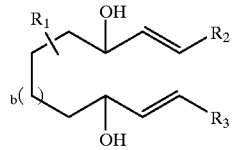

(II)

wherein b is an integer in a range from 1 to 6, $R_1$, $R_2$, and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

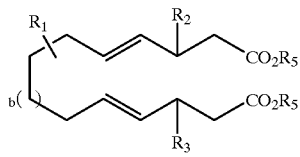

(III)

wherein b is an integer in a range from 1 to 6, $R_1$, $R_2$, $R_3$ are each independently a hydrogen atom or a $C_1$ to $C_4$ alkyl and $R_5$ is the alkyl group of said trialkylorthoacetate;

hydrogenating said linear bis-ester to form a saturated or mono-unsaturated linear bis-ester;

reacting said saturated or mono-unsaturated linear bis-ester via a Dieckmann cyclization pathway to form a β-ketoester; and hydrolyzing and decarboxylating said β-ketoester to form said saturated or mono-unsaturated macrocyclic ketone.

12. The method of claim 11 further comprising:

alkylating said β-ketoester prior to said hydrolyzing and decarboxylating step.

13. A method for synthesizing saturated or mono-unsaturated macrocyclic ketones having the general formula (IV):

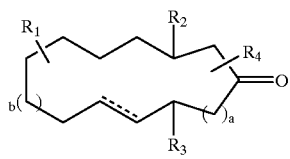

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting a 1,ω-di-Grignard reagent with an unsaturated aldehyde to form a bis-allyl alcohol of the following general formula (II):

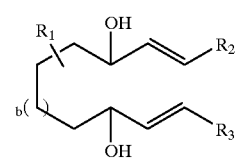

(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

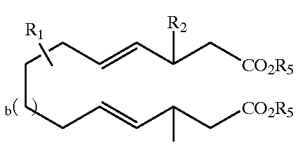

(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

hydrogenating said linear bis-ester to form a saturated or mono-unsaturated linear bis-ester;

performing an acyloin condensation of said saturated or mono-unsaturated linear bis-ester to form an α-hydroxyketone; and reducing said α-hydroxyketone to form said saturated or mono-unsaturated macrocyclic ketone.

14. A method for synthesizing saturated or mono-unsaturated macrocyclic ketones having the general formula (IV):

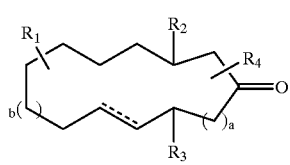

(IV)

wherein $R_1$, $R_2$ $R_3$, and $R_4$ are each independently a hydrogen atom or a $C_1$ to $C_4$ alkyl, a is the integer 1 or 2 and b is an integer in a range from 1 to 6, comprising:

reacting a 1,ω-di-Grignard reagent with an unsaturated aldehyde to form a bis-allyl alcohol of the following general formula (II):

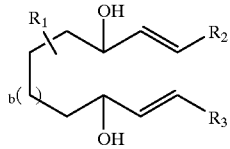
(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

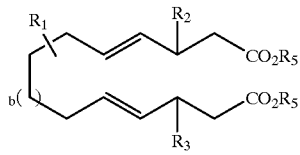
(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

hydrogenating said linear bis-ester to form a saturated or mono-unsaturated linear bis-ester;

reacting said saturated or mono-unsaturated linear bis-ester via a Dieckmann cyclization pathway to form a β-ketoester; and hydrolyzing and decarboxylating said β-ketoester to form said saturated or mono-unsaturated macrocyclic ketone.

15. The method of claim 14, further comprising:

alkylating said β-ketoester prior to said hydrolyzing and decarboxylating step.

16. A method for synthesizing saturated or mono-unsaturated macrocyclic ketones having the general formula (IV):

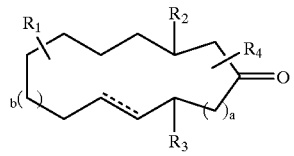
(IV)

wherein $R_1$, $R_2$, $R_3$ and $R_4$ are each independently a hydrogen atom or a $C_1$ to $C_4$ alkyl, a is the integer 1 or 2, and b is an integer in a range from 1 to 6, comprising:

reacting an optionally substituted 1,ω-dialdehyde with a Grignard reagent to form a bis-allyl alcohol of the following general formula (II):

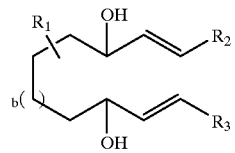
(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

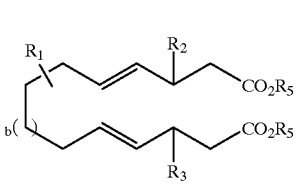
(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

performing an acyloin condensation of said linear bis-ester to form an α-hydroxyketone;

hydrogenating said α-hydroxyketone to form a saturated or mono-unsaturated α-hydroxyketone; and reducing said saturated or mono-unsaturated α-hydroxyketone to form said saturated or mono-unsaturated macrocyclic ketone.

17. A method for synthesizing saturated or mono-unsaturated macrocyclic ketones having the general formula (IV):

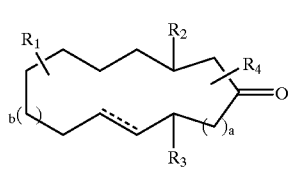
(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting an optionally substituted 1,ω-dialdehyde with a Grignard reagent to form a bis-allyl alcohol of the following general formula (II):

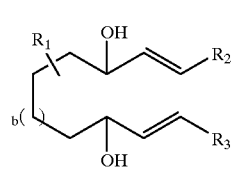
(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

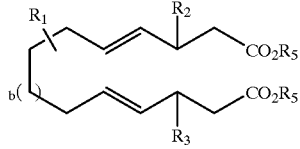
(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

reacting said linear bis-ester via a Dieckmann cyclization pathway to form a β-ketoester;

hydrogenating said β-ketoester to form a saturated or mono-unsaturated β-ketoester; and hydrolyzing and decarboxylating said saturated or mono-unsaturated β-ketoester to form a saturated or mono-unsaturated macrocyclic ketone.

18. The method according to claim 17, further comprising:
   alkylating said β-ketoester prior to said hydrogenation step.

19. The method according to claim 17, further comprising:
   alkylating said saturated or mono-unsaturated β-ketoester prior to said hydrolyzing and decarboxylating step.

20. A method for synthesizing saturated or mono-unsaturated macrocyclic ketones having the general formula (IV):

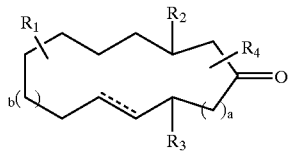
(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting a 1,ω-di-Grignard reagent with an unsaturated aldehyde to form a bis-allyl alcohol of the following general formula (II):

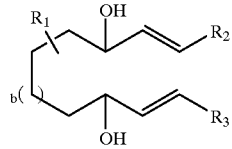
(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

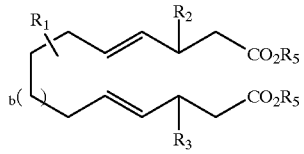
(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

performing an acyloin condensation of said linear bis-ester to form an α-hydroxyketone;

hydrogenating said α-hydroxyketone to form a saturated or mono-unsaturated α-hydroxyketone; and reducing said saturated or mono-unsaturated α-hydroxyketone to form said saturated or mono-unsaturated macrocyclic ketone.

21. A method for synthesizing saturated or mono-unsaturated macrocyclic ketones having the general formula (IV):

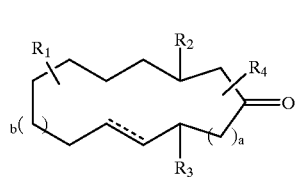
(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting a 1,ω-di-Grignard reagent with an unsaturated aldehyde to form a bis-allyl alcohol of the following general formula (II):

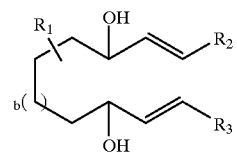
(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

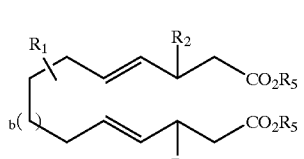
(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

reacting said linear bis-ester via a Dieckmann cyclization pathway to form a β-ketoester;

hydrogenating said β-ketoester to form a saturated or mono-unsaturated β-ketoester; and hydrolyzing and decarboxylating said saturated or mono-unsaturated β-ketoester to form said saturated or mono-unsaturated macrocyclic ketone.

22. The method of claim 21, further comprising:
alkylating said β-ketoester prior to said hydrogenation step.

23. The method of claim 21, further comprising:
alkylating said saturated or mono-unsaturated β-ketoester prior to said hydrolyzing and decarboxylating step.

24. A method for synthesizing saturated or mono-unsaturated macrocyclic ketones having the following general formula (IV):

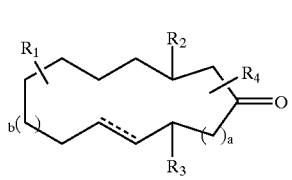

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting an optionally substituted 1,ω-dialdehyde with a Grignard reagent to form a bis-allyl alcohol of the following general formula (II):

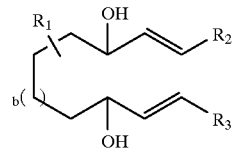

(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

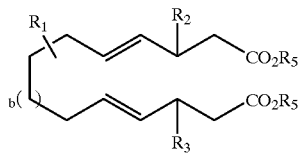

(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

performing an acyloin condensation of said linear bis-ester to form an α-hydroxyketone;

reducing said α-hydroxyketone to form a macrocyclic diene ketone; and hydrogenating said macrocyclic diene ketone to form said saturated or mono-unsaturated macrocyclic ketone.

25. A method for synthesizing saturated or mono-unsaturated macrocyclic ketones having the following general formula (IV):

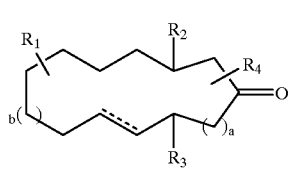

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting an optionally substituted 1,ω-dialdehyde with a Grignard reagent to form a bis-allyl alcohol of the following general formula (II):

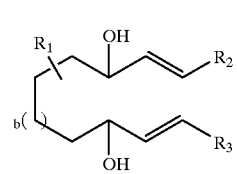

(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

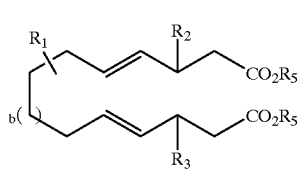

(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

reacting said linear bis-ester via a Dieckmann cyclization pathway to form a β-ketoester;

hydrolyzing and decarboxylating said β-ketoester to form a macrocyclic diene ketone; and hydrogenating said macrocyclic diene ketone to form said saturated or mono-unsaturated macrocyclic ketone.

26. The method of claim 25, further comprising:
alkylating said β-ketoester prior to said hydrolyzing and decarboxylating step.

27. A method for synthesizing saturated or mono-unsaturated macrocyclic ketones having the following general formula (IV):

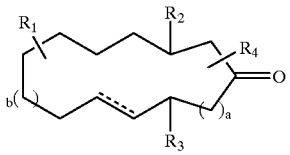

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting a 1,ω-di-Grignard reagent with an unsaturated aldehyde to form a bis-allyl alcohol of the following general formula (II):

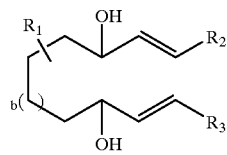

(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester having the following general formula (III):

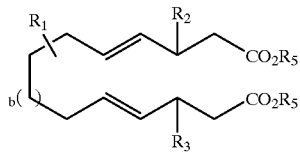

(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

performing an acyloin condensation of said linear bis-ester to form a α-hydroxyketone;

reducing said α-hydroxyketone to form a macrocyclic diene ketone; and hydrogenating said macrocyclic diene ketone to form said saturated or mono-unsaturated macrocyclic ketone.

28. A method for synthesizing saturated or mono-unsaturated macrocyclic ketones having the following general formula (IV):

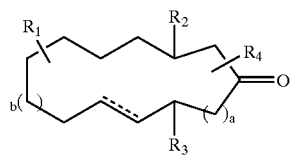

(IV)

wherein $R_1$, $R_2$, $R_3$ and $R_4$ are each independently a hydrogen atom or a $C_1$ to $C_4$ alkyl, a is the integer 1 or 2 and b is an integer in a range from 1 to 6, comprising:

reacting a 1,ω-di-Grignard reagent with an unsaturated aldehyde to form a bis-allyl alcohol of the following general formula (II):

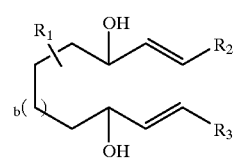

(II)

wherein b is an integer in a range from 1 to 6 and $R_1$, $R_2$ and $R_3$ are each independently a hydrogen atom or a $C_1$ to $C_4$ alkyl;

reacting said bis-allyl alcohol with a trialkylorthoacetate in the presence of acid catalysis resulting in a bis-Claisen rearrangement to form a linear bis-ester of the following general formula (III):

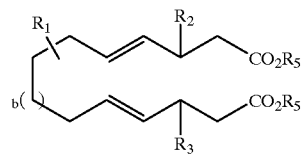

(III)

wherein b is an integer in a range from 1 to 6, $R_1$, $R_2$, and $R_3$ are each independently a hydrogen atom or a $C_1$ to $C_4$ alkyl, and $R_5$ is the alkyl group of said trialkylorthoacetate;

reacting said linear bis-ester via a Dieckmann cyclization pathway to form a β-ketoester;

hydrolyzing and decarboxylating said β-ketoester to form a macrocyclic diene ketone; and hydrogenating said macrocyclic diene ketone to form said saturated or mono-unsaturated macrocyclic ketone.

29. The method of claim 28, further comprising:

alkylating said β-ketoester prior to said hydrolyzing and decarboxylating step.

30. A fragrance composition comprising a compound of claim 1 in combination with at least one of a carrier and additional perfumery material.

31. A fragrance composition according to claim 30, further comprising a surfactant to form a product, whereby said product is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, a laundry detergent, a deodorant, an antiperspirant, a bleach, an air care product and a fabric softener.

32. A fragrance composition comprising a compound of claim 2 in combination with at least one of a carrier and additional perfumery material.

33. A fragrance composition according to claim 32, further comprising a surfactant to form a product, whereby said product is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, a laundry detergent, a deodorant, an antiperspirant, a bleach, an air care product and a fabric softener.

34. A fragrance composition comprising a compound of claim 3 in combination with at least one of a carrier and additional perfumery material.

35. A fragrance composition according to claim 34, further comprising a surfactant to form a product, whereby said product is effective to act as at least one of a cleaning agent, a skin cream, a hand and body lotion, a sunscreen agent, a hair conditioner, a water-based adhesive, a water-based paint, a shampoo, a dish washing liquid, a heavy duty cleaner, a general purpose cleaner, a liquid abrasive cleaner, a liquid soap, a laundry detergent, a deodorant, an antiperspirant, a bleach, an air care product and a fabric softener.

* * * * *